(12) United States Patent
Bruchman

(10) Patent No.: US 11,951,008 B2
(45) Date of Patent: *Apr. 9, 2024

(54) LEAFLET SUPPORT DEVICES AND METHODS OF MAKING AND USING THE SAME

(71) Applicant: EDWARDS LIFESCIENCES CORPORATION, Irvine, CA (US)

(72) Inventor: William C. Bruchman, Camp Verde, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 449 days.

This patent is subject to a terminal disclaimer.

(21) Appl. No.: 17/038,022

(22) Filed: Sep. 30, 2020

(65) Prior Publication Data

US 2021/0059817 A1 Mar. 4, 2021

Related U.S. Application Data

(63) Continuation of application No. 16/024,252, filed on Jun. 29, 2018, now Pat. No. 10,806,576, which is a (Continued)

(51) Int. Cl.
*A61F 2/24* (2006.01)
*A61L 27/14* (2006.01)
(Continued)

(52) U.S. Cl.
CPC .......... *A61F 2/2445* (2013.01); *A61F 2/2403* (2013.01); *A61F 2/2442* (2013.01);
(Continued)

(58) Field of Classification Search
CPC .... A61F 2/2442; A61F 2/2415; A61F 2/2418; A61F 2/2412
See application file for complete search history.

(56) References Cited

U.S. PATENT DOCUMENTS 4,265,694 A * 5/1981 Boretos ................. A61F 2/2412
623/901
5,708,044 A 1/1998 Branca
(Continued)

FOREIGN PATENT DOCUMENTS

JP 2005-504577 A 2/2005
JP 2007-518492 A 7/2007
(Continued)

OTHER PUBLICATIONS

Communication relating to the results of the Partial International Search Report for PCT/US2016/055644 dated Jan. 31, 2017, corresponding to U.S. Appl. No. 15/286,031, 4 pages.
(Continued)

*Primary Examiner* — Jason-Dennis N Stewart
(74) *Attorney, Agent, or Firm* — Jeffrey B. Haendler; KLARQUIST SPARKMAN, LLP

(57) ABSTRACT

Described embodiments are directed toward centrally-opening leaflet support devices having a frame and one or more support leaflets coupled to the frame forming a hinge where coupled. The described support leaflets have one or more stiffer regions that facilitate the function of a support leaflet to decrease or prevent prolapse of a native valve leaflet. Methods of making and using such valve devices are also described amongst others.

21 Claims, 22 Drawing Sheets

Related U.S. Application Data continuation of application No. 15/286,031, filed on Oct. 5, 2016, now Pat. No. 10,022,223.

(60) Provisional application No. 62/237,856, filed on Oct. 6, 2015.

(51) Int. Cl.
  *A61L 27/16* (2006.01)
  *A61L 27/40* (2006.01)

(52) U.S. Cl.
  CPC .......... *A61F 2/2454* (2013.01); *A61F 2/2463* (2013.01); *A61L 27/14* (2013.01); *A61L 27/16* (2013.01); *A61L 27/40* (2013.01); *A61F 2220/0008* (2013.01); *A61F 2220/0016* (2013.01); *A61F 2240/001* (2013.01); *A61F 2250/0018* (2013.01); *A61F 2250/0039* (2013.01)

(56) References Cited

U.S. PATENT DOCUMENTS

| | | |
|---|---|---|
| 6,419,695 B1 | 7/2002 | Gabbay |
| 6,541,589 B1 | 4/2003 | Baillie |
| 7,291,168 B2 | 11/2007 | Macoviak et al. |
| 7,306,729 B2 | 12/2007 | Bacino et al. |
| 7,462,675 B2 | 12/2008 | Chang et al. |
| 7,531,611 B2 | 5/2009 | Sabol et al. |
| 8,262,725 B2 | 9/2012 | Subramanian |
| 8,480,732 B2 | 7/2013 | Subramanian |
| 8,637,144 B2 | 1/2014 | Ford |
| 8,956,406 B2 | 2/2015 | Subramanian et al. |
| 8,961,597 B2 | 2/2015 | Subramanian et al. |
| 8,961,599 B2 | 2/2015 | Bruchman et al. |
| 9,139,669 B2 | 9/2015 | Xu et al. |
| 9,168,137 B2 | 10/2015 | Subramanian et al. |
| 9,452,048 B2 | 9/2016 | O'Beirne et al. |
| 10,022,223 B2 | 7/2018 | Bruchman |
| 10,806,576 B2 | 10/2020 | Bruchman |
| 2003/0078652 A1* | 4/2003 | Sutherland ............ A61F 2/2412 623/2.12 |
| 2004/0127981 A1 | 7/2004 | Rahdert et al. |
| 2004/0138745 A1 | 7/2004 | Macoviak et al. |
| 2004/0162610 A1 | 8/2004 | Liska et al. |
| 2005/0004668 A1 | 1/2005 | Aklog et al. |
| 2005/0038508 A1 | 2/2005 | Gabbay |
| 2005/0107871 A1 | 5/2005 | Realyvasquez et al. |
| 2005/0159810 A1 | 7/2005 | Filsoufi |
| 2008/0243245 A1 | 10/2008 | Thambar et al. |
| 2009/0228099 A1 | 9/2009 | Rahdert et al. |
| 2010/0298930 A1 | 11/2010 | Orlov |
| 2010/0318184 A1 | 12/2010 | Spence |
| 2011/0066233 A1 | 3/2011 | Thornton et al. |
| 2012/0078356 A1 | 3/2012 | Fish et al. |
| 2012/0185040 A1 | 7/2012 | Rahdert et al. |
| 2012/0323315 A1 | 12/2012 | Bruchman et al. |
| 2013/0023985 A1 | 1/2013 | Khairkhahan et al. |
| 2014/0172077 A1 | 6/2014 | Bruchman et al. |
| 2015/0094802 A1 | 4/2015 | Buchbinder et al. |
| 2015/0100116 A1 | 4/2015 | Mohl et al. |
| 2017/0105839 A1 | 4/2017 | Subramanian et al. |
| 2018/0303611 A1 | 10/2018 | Bruchman |
| 2019/0117838 A1* | 4/2019 | Frey ...................... A61L 27/225 |

FOREIGN PATENT DOCUMENTS

| | | |
|---|---|---|
| WO | 03/28558 A2 | 4/2003 |
| WO | 2005/027797 A1 | 3/2005 |
| WO | 2005/069875 A2 | 8/2005 |
| WO | 2009/094585 A2 | 7/2009 |
| WO | 2013/076724 A2 | 5/2013 |
| WO | 2014/149319 A1 | 9/2014 |
| WO | 2014/207575 A2 | 12/2014 |

OTHER PUBLICATIONS

International Preliminary Report on Patentability received for PCT Patent Application No. PCT/US2016/055644, dated Apr. 19, 2018, 13 pages.

International Search Report and Written Opinion of PCT/US2016/055644, dated Jun. 2, 2017, 20 pages.

* cited by examiner

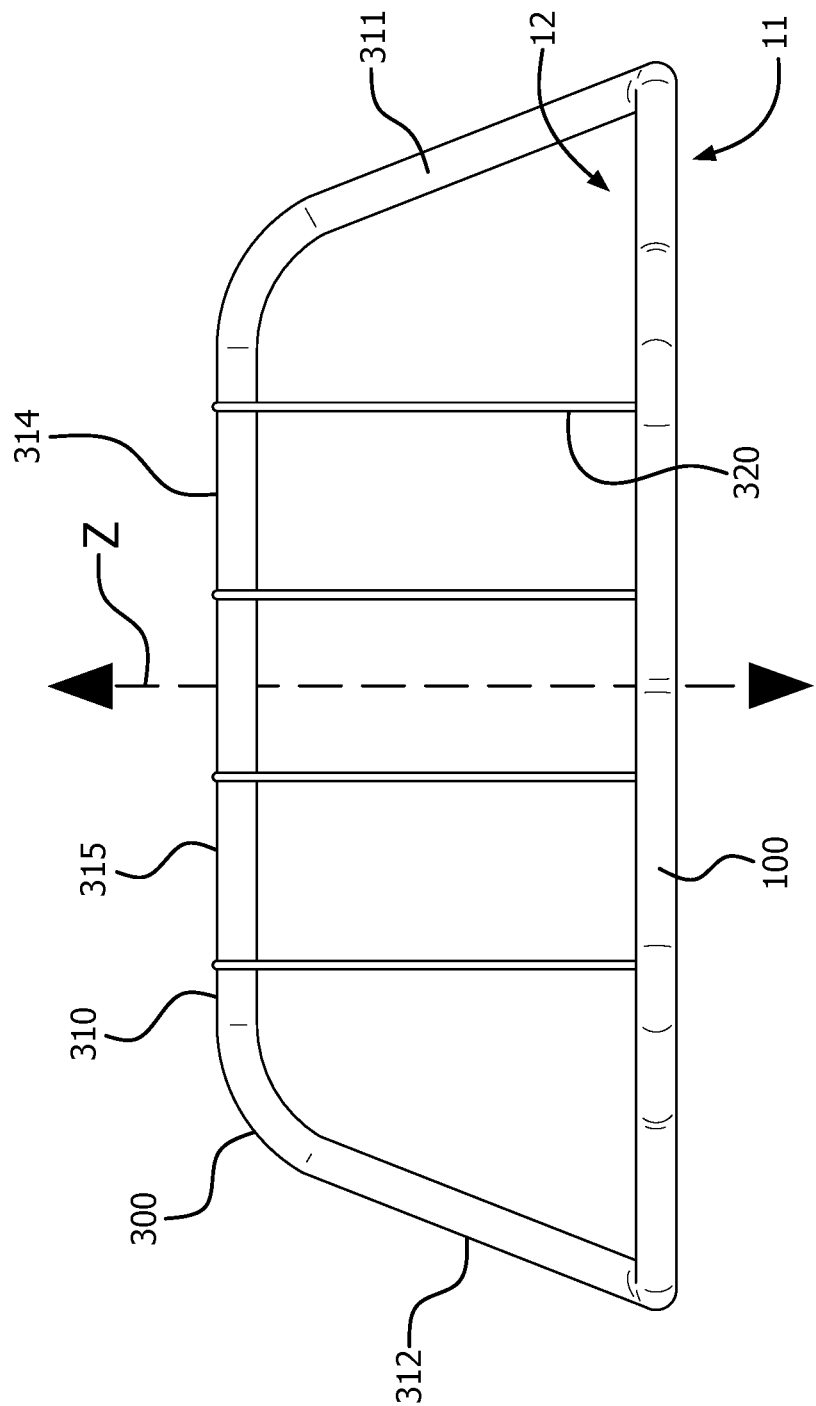

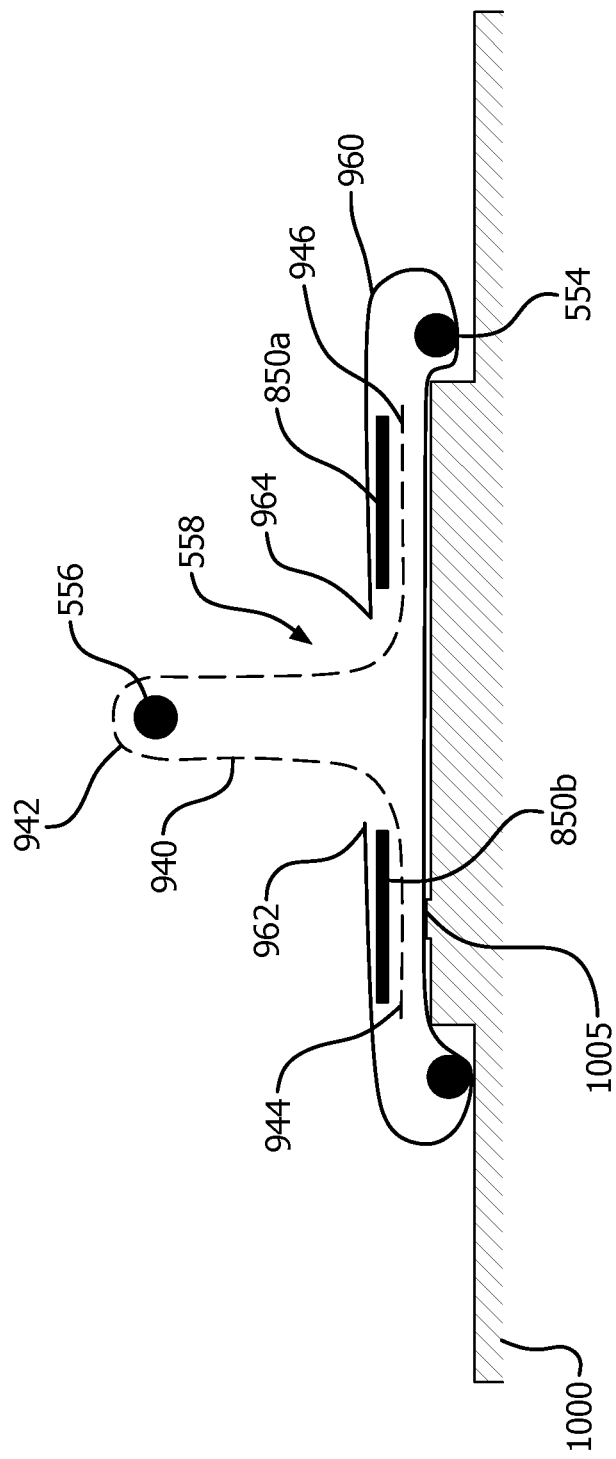

LEAFLET SUPPORT DEVICES AND METHODS OF MAKING AND USING THE SAME

CROSS-REFERENCE TO RELATED APPLICATION

This application is a continuation of U.S. patent application Ser. No. 16/024,252, filed Jun. 29, 2018, which is a continuation of U.S. patent application Ser. No. 15/286,031, filed Oct. 5, 2016, now U.S. Pat. No. 10,022,223, issued Jul. 17, 2018, which claims the benefit of U.S. Provisional Application 62/237,856, filed Oct. 6, 2015, all of which are incorporated herein by reference in their entireties for all purposes.

FIELD

The present disclosure relates generally to valve leaflet support devices, in particular heart valve leaflet support devices that are useful for improving performance of incompetent atrioventricular leaflets.

BACKGROUND

The leaflets of atrioventricular valves (mitral and tricuspid) are thin, diaphanous structures that rely on a system of long, thin, cord-like supports to maintain competence of the valve in the loaded condition. These supports are appropriately termed the chordae tendinae, and attach the papillary muscles to the valve leaflets.

Mitral valve dysfunction can be broadly grouped into four categories. Type I has normal leaflet motion, but regurgitation arises from annular dilation, or more rarely, leaflet perforation. Type II displays excessive leaflet motion and is commonly termed prolapse. It is the condition in which one or both leaflets are misaligned, and it arises from chordae tendinae or papillary muscle stretching or degeneration. Type IIIa leaflets have normal alignment but reduced motion due to thickening of the leaflet(s) or subannular structures. Type IIIb is a consequence of ventricular dilation. As the ventricle dilates, the papillary muscles are displaced laterally causing leaflet tethering and subsequent regurgitation.

When the chordae tendinae degenerate and become stretched, leaflet prolapse can arise and the leaflet(s) can misalign under systolic loading.

Atrioventricular valve prolapse is a common cardiac disease; in most cases, it is asymptomatic, but when the leaflet misalignment becomes severe enough, regurgitation results. In the majority of cases, the regurgitation arises from a misalignment of the leaflets in which one of the leaflets displaces to a position superior to the other, allowing flow to bypass the leaflets, but the misalignment can also be the result of two prolapsed leaflets. To illustrate, a side cross-sectional view of a normal valve 5a is shown in FIG. 1A, a valve 5b with one prolapsed leaflet 7 due to dysfunctional chordae tendinae 6 in FIG. 1B, and a valve 5c with two prolapsed leaflets 7 in FIG. 1C.

Heretofore, when the atrioventricular valves required replacement, the leaflets were excised, and commonly, the same prostheses as used for the semilunar valves, either mechanical or bioprosthetic implanted, despite the low-profile nature of the AV valves. This approach, though it has met with some success, ignores the unique anatomy/pathology of the AV valves.

In recent years, mitral valve repair has shown initial good success, but it is an extremely invasive and complicated procedure, typically performed only in university hospitals. Leaflet resection involves cutting out the extra tissue and sewing the remnants back together, cardiopulmonary bypass is required, and experience has shown that the initial good result does not necessarily persist. Another procedure of similar complexity is to replace stretched or broken chordae tendinae with suture of expanded polytetrafluoroethylene (ePTFE). Thus, new ways of improving or restoring native valve function is needed.

SUMMARY

Described embodiments are directed to devices, systems, and methods for leaflet support to restore leaflet coaptation. The leaflet support devices described herein are intended primarily for use in the mitral and tricuspid valves. Each of the four mitral valve categories of dysfunction can be treated with various embodiments described in the present disclosure. One aspect of the embodiments is that the native leaflets and sub-valvular structures remain intact and coaptation is restored.

The approach taken with embodiments described in the present disclosure is to leave the entire valvular and sub-valvular apparatus in place and use a leaflet support device to restore competence to the native valve. In type I or type II pathologies, embodiments described in the present disclosure guide the leaflet to restore coaptation between the native coaptation surfaces. In type IIIa and IIIb pathologies, embodiments described in the present disclosure ensure that the coaptation can occur between polymer surfaces or between one native leaflet and one polymer surface. In some embodiments, the leaflet support device is implanted through transcatheter delivery so that the patient is spared the morbidity associated with open-heart surgery.

The articles of this invention are central-flow frames with one or more support leaflets. In some embodiments, such articles can be compressed to a smaller diameter for catheter delivery. The leaflets can be coupled to a frame and anchored within the inflow tract. The leaflets can open as far as is permitted by the patient's anatomy, but the closing excursion is controlled by the extent of support leaflet travel.

In some embodiments, the leaflets are also supported in the central portion from an arched support placed between the leaflets. In such embodiments, the prosthetic leaflet travel can be limited by element(s) that attach the leaflet free edge to a suspending structure; this structure is also attached to the frame and extends between the leaflets to the outflow side of the native valve. In other embodiments, the support leaflets can close against a coplanar support extending across the central opening of the surrounding frame. In another embodiment, the leaflet(s) is attached to the base of a frame that is operable to be placed into the atrium of the heart, wherein the leaflet(s) opens with the native leaflets, and closes against the base of the frame.

Described embodiments include a leaflet support device comprising: a frame at least partially defining a central opening through which blood flows during use, wherein the frame is configured to be coupled with an annulus of an atrioventricular valve or with an atrium at a level of or adjacent to the annulus; one or more support leaflets, each support leaflet comprising a leaflet attachment region coupled to the frame and a free edge opposite the leaflet attachment region, each support leaflet being configured to pivot about the respective leaflet attachment region to move between an open and a closed position, and each support leaflet being configured to support at least a portion of an atrial-facing surface of an atrioventricular valve leaflet when in the closed position; and one or more limiters coupled to the frame. Each limiter can be configured to limit the degree of movement of at least one of the one or more support leaflets when the one or more support leaflets are moving from the open to the closed position. Moreover, the support leaflet can be configured such that each support leaflet free edge moves correspondingly with an atrioventricular valve leaflet to the open position and moves correspondingly with the atrioventricular valve leaflet to the closed position during use. Each support leaflet together with the one or more limiters is configured to restrict movement of the atrioventricular valve leaflet so as to decrease or prevent prolapse of the atrioventricular valve leaflet. In some embodiments, the atrioventricular valve is a mitral valve.

The leaflet support device can comprise a single support leaflet or two or more support leaflets. In some embodiments, the support leaflet comprises a support leaflet base that extends adjacent to the leaflet attachment region, each support leaflet base comprising a flexible material that is configured to flex so that the support leaflet moves to the open position as blood begins to flow through the valve. In some embodiments, the frame has a rounded shape that defines the central opening or wherein a portion of the frame comprises an arc that partially defines the central opening.

In some embodiments, each support leaflet comprises one or more stiffer regions with a stiffness that is greater than an adjacent region. In some embodiments, the one or more stiffer regions with greater stiffness extend across at least 70% of a dimension of the support leaflet wherein the dimension is substantially transverse to blood flow. In some embodiments, the one or more stiffer regions with greater stiffness extend along a length that is in the same direction as a line defined by native leaflet coaptation. In some embodiments, the one or more stiffer regions with greater stiffness comprise one or more reinforcements configured to impart a stiffness to at least a portion of the support leaflet sufficient to support the atrioventricular valve leaflet so as to decrease or prevent prolapse of the atrioventricular valve leaflet. In some embodiments, each support leaflet comprises a laminate material comprising layers, and each reinforcement is disposed between the layers. In some embodiments, each reinforcement is a wire with a serpentine conformation, or it defines an open framework extending along a region between the leaflet attachment region and the free edge.

In some embodiments, the limiter comprises a bridge extending from sides of and across the central opening of the frame, wherein the bridge is configured to resist movement of at least one support leaflet. In some embodiments, the bridge is configured to extend across the region of greater stiffness, when the support leaflet is in the closed position. In some embodiments, the bridge is closer to the leaflet attachment region than to the free edge of the same leaflet. In some embodiments, the bridge comprises an elliptical cross-sectional profile. In some embodiments, the limiter comprises one or more tethers, where each tether is coupled to the bridge and to at least one of the one or more support leaflets. In some embodiments, the bridge comprises an intermediate portion that is spaced apart from the central opening of the frame. In some embodiments, each tether is coupled to the free edge of at least one of the one or more support leaflets. In some embodiments, each support leaflet comprises a laminate material comprising layers and a portion of each tether is disposed between the layers.

In some embodiments, each support leaflet is generally coplanar when in the closed position with the central opening through which blood flows, h some embodiments, the frame is configured to be resiliently compressible in a radial direction such that the frame, when in a compressed state during use, urges against the annulus or the atrium to couple the frame to the annulus or the atrium, h some embodiments, at least a region of the frame defines undulations and wherein the frame defines a closed-shape. In some embodiments, the undulations extend in a radial direction. In some embodiments, the frame comprises an outer layer of material defining a frame surface, and the outer layer of material comprises a fluoropolymer. In some embodiments, the outer layer of material is the same material as a portion of the support leaflet, such as the support leaflet base. In some embodiments, the frame comprises one or more tissue anchors configured to engage with the annulus of the atrioventricular valve or with the atrium at the level of or adjacent to the annulus. In some embodiments, the support leaflet comprises anchors configured to couple to an atrial-facing surface of an atrioventricular valve leaflet. In some embodiments, the leaflet support device is configured to have an operating configuration and a delivery configuration for delivery via a catheter.

In accordance with another embodiment, a leaflet support device, comprises a frame and one or more support leaflets. The frame defines a shape defined by a tubular member bisected by a flat ring at a base of the tubular member. The tubular member defines a tubular member central axis and has a decreasing taper from a first end to the base and defines a tubular member central opening at the base through which blood flows during use. The tubular member is configured to conform to and be coupled with an atrial side of a heart adjacent to an atrioventricular valve. The flat ring defining a ring central axis has a second frame central opening through which blood flows during use. The flat ring is substantially perpendicular to and coaxial with the tubular member central axis. The flat ring defines an inner portion that extends into the tubular member central opening and an outer portion that extends away from the tubular member central opening. The outer portion is configured to rest against a ventricular side of an annulus of the atrioventricular valve. Each of the one or more support leaflets comprise a leaflet attachment region either coupled to the flat ring or coupled to the base adjacent the flat ring and a free edge opposite the leaflet attachment region. Each support leaflet is configured to pivot about the respective leaflet attachment region to move between an open and a closed position. When in the closed position, the support leaflet lies adjacent a ventricular side of the second frame. Each support leaflet is configured to support at least a portion of an atrial-facing surface of an atrioventricular valve leaflet when in the closed position. The inner portion of the second frame is configured to limit the degree of movement of at least one of the one or more support leaflets when the one or more support leaflets are moving from the open to the closed position, wherein the support leaflet coapts against the ventricular side of the inner portion of the second frame. Each support leaflet is configured such that the support leaflet free edge moves correspondingly with an atrioventricular valve leaflet to the open position and moves correspondingly with the atrioventricular valve leaflet to the closed position during use.

In other embodiments, the leaflet support device, comprises a first frame, a second frame and one or more support leaflets. The first frame defines a tubular shape defining a first frame central axis and having a decreasing taper from a first frame first end to a base and defining a first frame central opening at the base through which blood flows during use. The first frame is configured to conform to and be coupled with an atrial side of a heart adjacent to an atrioventricular valve. The second frame defines a flat ring shape defining a second frame central axis having a second frame central opening through which blood flows during use. The second frame is coupled to the first frame at the base and substantially perpendicular to and coaxial with the first frame central axis. The second frame defines an inner portion that extends into the first frame central opening and an outer portion that extends away from the first frame central opening. The outer portion is configured to rest against a ventricular side of an annulus of the atrioventricular valve. Each support leaflet comprises a leaflet attachment region coupled to the second frame or coupled to the base adjacent the second frame and a free edge opposite the leaflet attachment region. Each support leaflet is configured to pivot about the respective leaflet attachment region to move between an open and a closed position. While in the closed position the support leaflet lies adjacent a ventricular side of the second frame, wherein each support leaflet is configured to support at least a portion of an atrial-facing surface of an atrioventricular valve leaflet when in the closed position. The inner portion of the second frame is configured to limit the degree of movement of at least one of the one or more support leaflets when the one or more support leaflets are moving from the open to the closed position, wherein each support leaflet coapts against the ventricular side of the inner portion of the second frame. Each support leaflet is configured such that the support leaflet free edge moves correspondingly with an atrioventricular valve leaflet to the open position and moves correspondingly with the atrioventricular valve leaflet to the closed position during use.

In those pathologies that have dilation of the mitral annulus or the right ventricle itself, additional coaptation surfaces can be provided in accordance with embodiments. The additional coaptation surfaces are typically on the posterior side of the valve and forms a surface against which the anterior leaflet can coapt.

Other embodiments include a method of delivering the leaflet support device via a catheter. In some embodiments, the method comprises providing a delivery catheter having an expandable leaflet support device in a collapsed state constrained over or within the delivery catheter at a distal end of the delivery catheter; passing the delivery catheter through the introducer sheath and into valve annulus; positioning the distal end of the delivery catheter so that the leaflet support device is properly positioned and oriented within the valve annulus; and expanding the leaflet support device at the valve annulus into contact therewith.

Yet other embodiments include a method of making a leaflet support device. In some embodiments, a method of making can comprise coupling one or more support leaflets to a frame defining a central opening such that the support leaflets are capable of extending into the central opening of the frame. In some embodiments, a method of making can comprise providing a frame with a bridge coupled thereto; folding a leaflet support material around the frame such that the frame is disposed in a fold of the leaflet support material and the support leaflet will comprise a first layer of film and a second layer of film; placing a reinforcement between the first layer and second layer of film; and laminating the first layer and the second layer together to form the support leaflet. In some embodiments, the method can further comprise placing a tether portion between the first layer and the second layer such that the tether exits the leaflet free edge and coupling the tether to the bridge.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The features and advantages of the present disclosure will become more apparent from the detailed description set forth below when taken in conjunction with the drawings.

FIG. 2C is a side view of the leaflet support device of FIG. 2A;

FIG. 10A is a cross-sectional, schematic view of a device assembly jig with the components layered on the jig as further described in the Examples;

DETAILED DESCRIPTION OF THE ILLUSTRATED EMBODIMENTS

Figure 1C:
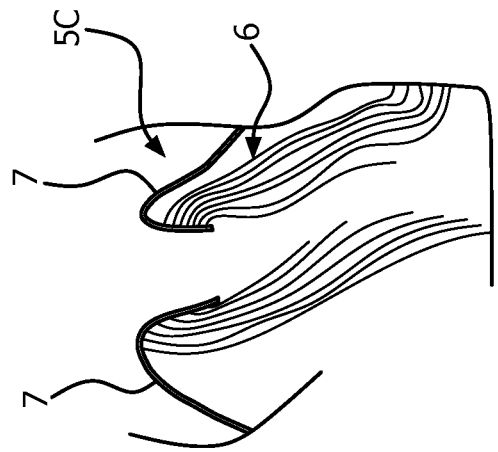
FIG. 1C is a cross-sectional, schematic view of an atrioventricular valve with two prolapsed leaflets such that coaptation is not occurring during systole representative of Types I, IIIa and IIIb pathology.
Figure 1B:
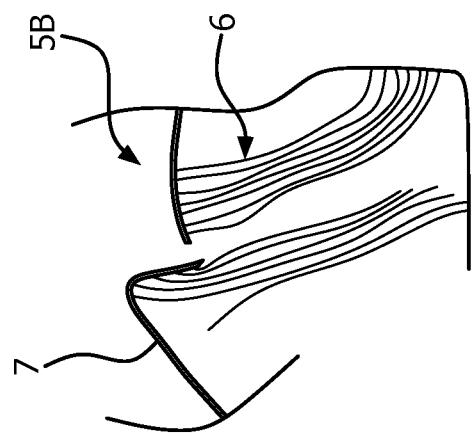
FIG. 1B is a cross-sectional, schematic view of an atrioventricular valve with a single prolapsed leaflet that is misaligned such that coaptation is not occurring during systole representative of Type II pathology.
Figure 1A:
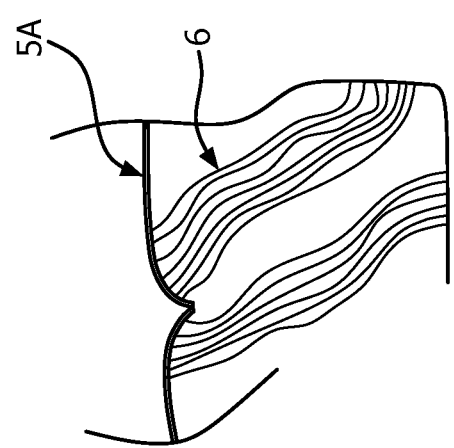
FIG. 1A is a cross-sectional, schematic view of a normal atrioventricular valve during systole.

Persons skilled in the art will readily appreciate that various aspects of the present disclosure can be realized by any number of methods and apparatuses configured to perform the intended functions. Stated differently, other methods and apparatuses can be incorporated herein to perform the intended functions. Furthermore, a structure that is capable performing a function or that is configured in a certain way is capable or configured in at least that way, but may also be capable or configured in ways that are not listed. It should also be noted that the accompanying drawing figures referred to herein are not all drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with leaflet support device, particularly for cardiac applications and particularly for atrioventricular valve applications. Embodiments within the scope of this disclosure can be applied toward any cardiac or non-cardiac valve or mechanism of similar structure and/or function.

The term "membrane" as used herein refers to a sheet of material comprising a single composition, such as, but not limited to, expanded fluoropolymer.

The term "composite material" as used herein refers to a combination of a membrane, such as, but not limited to, expanded fluoropolymer, and an elastomer, such as, but not limited to, a fluoroelastomer. The elastomer may be present within a porous structure of the membrane, coated on one or both sides of the membrane or a combination of coated on and present within the membrane.

The term "laminate" as used herein refers to multiple layers of membrane, composite material, or other materials, such as elastomer, and combinations thereof.

The term "film" as used herein generically refers to one or more of the membrane, composite material, or laminate.

The term "leaflet support device" as used herein refers to a device configured to provide load-sharing support to the pre-existing leaflets, e.g., native leaflets. Components of the device can include a frame, a limiter, and a support leaflet.

The term "frame" as used herein refers to a component that completely or partially defines a central opening through which blood is intended to flow during use.

The term "limiter" as used herein refers to a component or a combination of components that are configured to limit the degree of movement of support leaflet when pivoting between the open to close position. It is understood that, in some embodiments, a limiter may also limit the movement of support leaflet when pivoting between the closed to open position.

The term "bridge" as used herein refers to a component of the limiter that is coupled to the frame and extends across the central opening of the frame.

The term "support leaflet" as used herein refers to a component of the leaflet support device that is operable to move between an open and closed position under the influence of a pressure differential and/or the action of the native leaflet and is configured to support the native leaflet. In an open position, blood can flow through the frame. In a closed position, the support leaflet extends generally in a plane that is transverse to the direction of intended blood flow and the native leaflet generally prevents retrograde flow of blood through the native valve. The pressure differential in the blood is caused, for example, by the contraction of a ventricle or atrium of the heart. The pressure differential typically results from a fluid pressure building up on one side of the native leaflets when closed. As the pressure on an inflow side of the native valve rises above the pressure on the outflow side of the native valve, the native leaflets and support leaflets will open and blood flows therethrough. As blood flows through the native valve into a neighboring chamber or blood vessel, the pressure on the inflow side equalizes with the pressure on the outflow side. As the pressure on the outflow side of the native valve rises above the blood pressure on the inflow side of the native valve, the native leaflet and support leaflet return to the closed position generally preventing retrograde flow of blood through the native valve.

The term "support leaflet base" as used herein refers to the portion of the support leaflet that meets the frame. The term "support leaflet free edge" as used herein refers to an edge of the leaflet that is opposite the support leaflet base.

The term "inflow-facing surface" refers to a surface that generally faces a direction that would be opposite to a direction of intended or actual fluid flow, and the term "outflow-facing surface" refers to a surface that generally faces a direction that would be aligned with the direction of intended or actual fluid flow. For leaflets as described herein, the general direction that a surface faces is ascertained when the leaflet is in a closed position. In the context of an atrioventricular valve, the inflow-facing surface is the atrial-facing surface, and the outflow-facing surface is the ventricular-facing surface. The terms do not necessarily mean that the described feature or object will be in contact with a flowing fluid.

The terms "native heart valve annulus" and "valve annulus" refer to an anatomical structure defining a central opening that supports the leaflets of the valve.

As used herein, "couple" means to join, connect, attach, adhere, affix, or bond, whether directly or indirectly, and whether permanently or temporarily.

The terms "a" and "an" are defined as one or more unless this disclosure explicitly requires otherwise.

The terms "substantially," "approximately" and "about" are defined as being largely but not necessarily wholly what is specified (and include wholly what is specified) as understood by one of ordinary skill in the art.

The preposition "between," when used to define a range of values (e.g., between x and y) means that the range includes the end points (e.g., x and y) of the given range and the values between the end points.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, any of the present devices, systems, and methods that "comprises," "has," "includes," or "contains" one or more elements possesses those one or more elements, but is not limited to possessing only those one or more elements.

Likewise, an element of a device, system, or method that "comprises," "has," "includes," or "contains" one or more features possesses those one or more features, but is not limited to possessing only those one or more features.

Any of the present devices, systems, and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Embodiments herein include various devices, systems, and methods for a leaflet support device suitable for surgical and transcatheter placement for treating, such as, but not limited to, dilatation of the annulus or ventricle, valve leaflet prolapse either by itself or in conjunction with other pathological conditions of the valve. Devices in accordance with this disclosure not intended to replace a pre-existing valve structure but rather improve its competence by providing load-sharing support to the pre-existing leaflets, e.g., native leaflets. The leaflet support device comprises one or more leaflet supports that are operable to move with the native leaflets during systole and diastole cycles, yet the leaflet supports are limited in the range of movement when pivoting between the open to closed position, e.g., movement is impeded late in the systole cycle of a mitral valve. In some embodiments, additional artificial surfaces are employed that are operable to coapt against themselves or against a native leaflet surface; said artificial surfaces are also used to reduce the diameter of the orifice so as to restore coaptation.

In accordance with a present disclosure, a leaflet support device can comprise a frame at least partially defining a central opening through which blood flows during use. The frame is configured to be coupled with an annulus of a valve (e.g., an atrioventricular valve) or with an atrium at the level of or adjacent to the annulus. For example, the frame can be configured to be resiliently compressible in a radial direction such that the frame, during use, urges against the annulus or the atrium to couple the frame to the annulus or the atrium.

The leaflet support device also comprises one or more support leaflets that are coupled to the frame. Each support leaflet can have a leaflet attachment region, a leaflet base, and a belly region terminating at a support leaflet free edge. The leaflet attachment region contacts the frame and the leaflet base is adjacent this region of contact. In the belly region, a leaflet support can have a stiffened region, such as through the use of a reinforcement piece. The support leaflet, through the use of less stiff and stiffer regions, provides sufficient support to the native leaflets but the configuration of the less stiff and stiffer regions also allows the support leaflet to flex at the leaflet base and follow the movements of the native leaflets. By moving with the native leaflet, the support leaflets are less disruptive of the blood flow pattern that would be observed pre-implantation. For atrioventricular valves, the frame and a support leaflet can be configured such that the support leaflet coupled to the frame extends generally in a plane that is transverse to the direction of intended blood flow when in a closed position.

The leaflet support device also comprises one or more limiters. Through the use of limiters, the leaflet support movement from open to closed is limited. The limiter can be one or more components that, together with the support leaflet, share some of the load placed on the native leaflet when blocking flow, e.g., late in the systole cycle for a mitral leaflet.

Figure 2A:
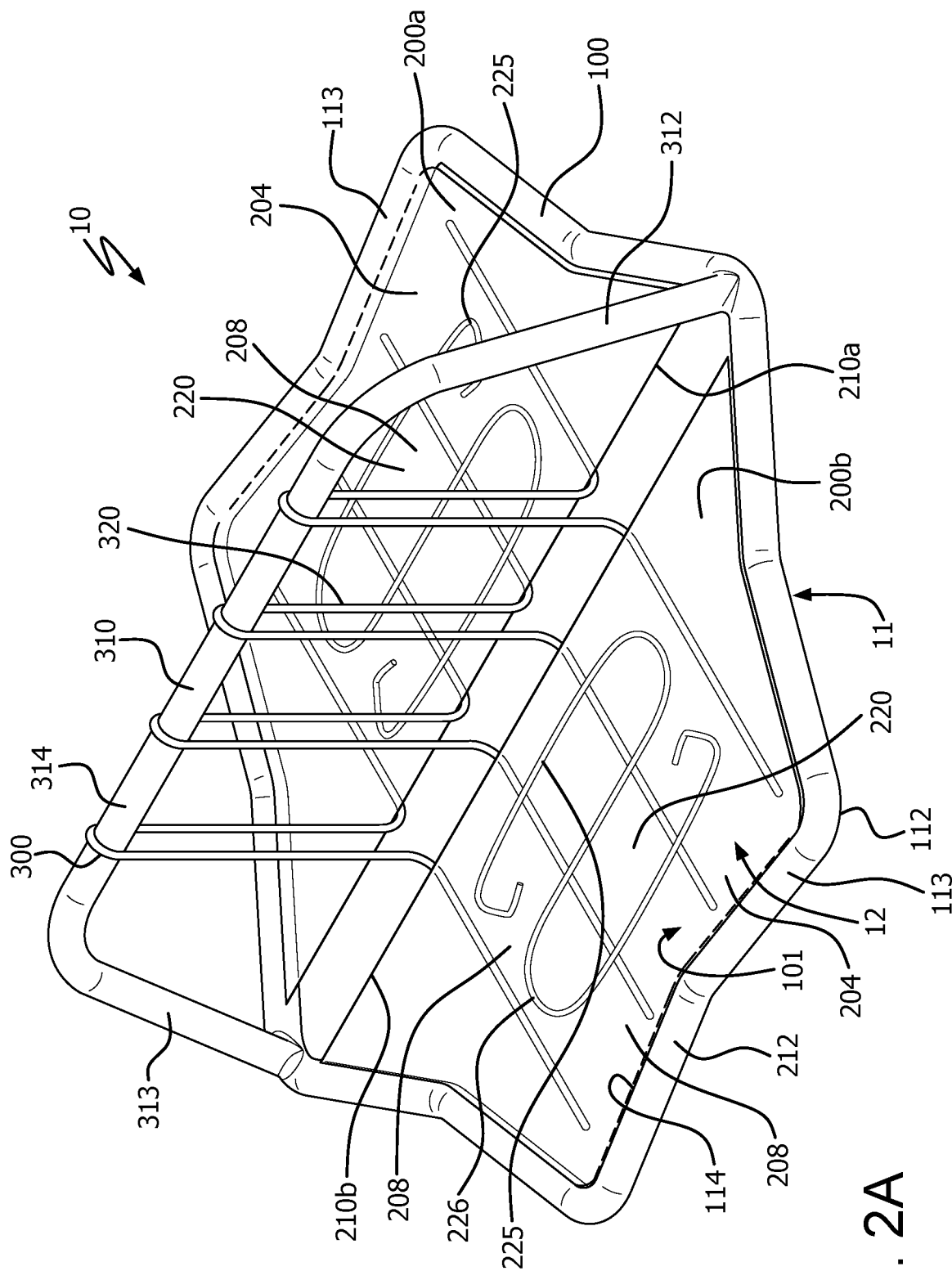
FIG. 2A is a perspective view of a leaflet support device in accordance with an embodiment, where the leaflet support is in a closed position.
Figure 2B:
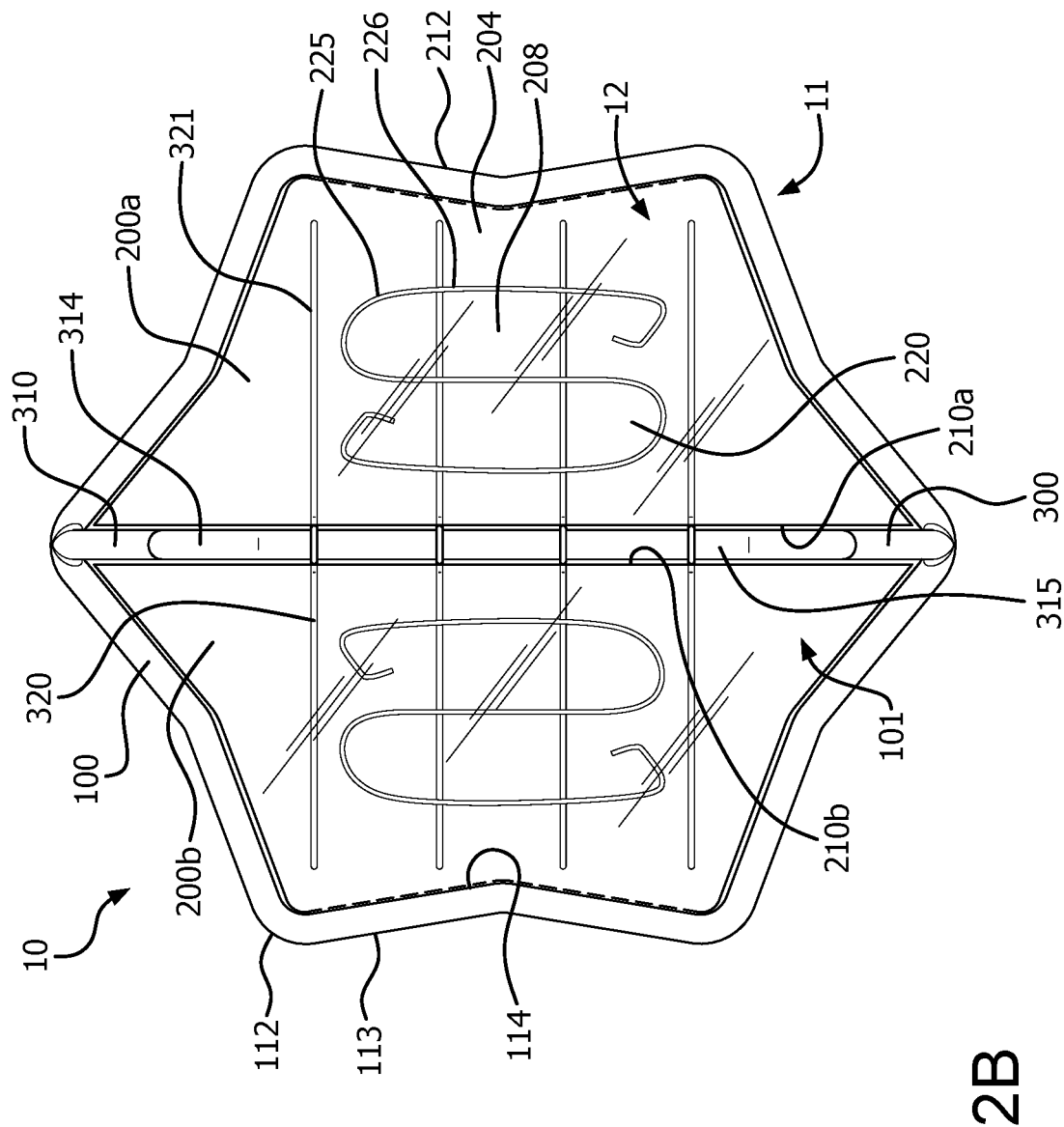
FIG. 2B is a top view looking in the upstream direction of the leaflet support device of FIG. 2A.
Figure 2D:
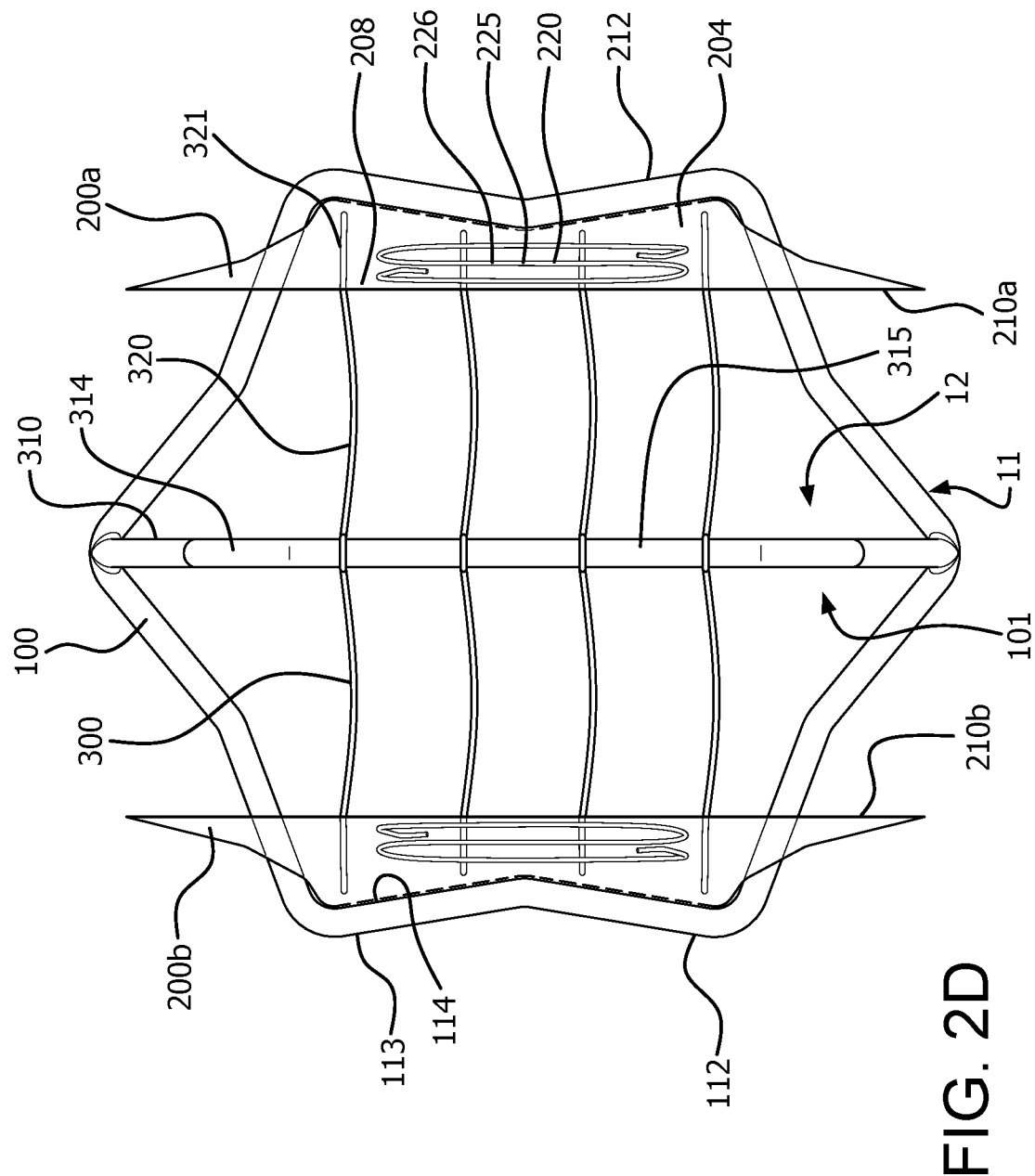
FIG. 2D is a top view looking in the upstream direction of the leaflet support device of FIG. 1A, except with the leaflet supports in an open position.

FIG. 2A is a perspective view, FIG. 2B is a top view looking in the upstream direction, and FIG. 2C is a side view of a leaflet support device 10, in accordance with an embodiment. The components of the leaflet support device 10 that are visible in FIGS. 2A to 2C include a frame 100, a first support leaflet 200a, a second support leaflet 200b (referred to collectively as "support leaflets 200"), and a limiter 300 comprising a bridge 310 and a plurality of tethers 320. The frame 100 defines a central opening 101 through which blood flows during use. FIGS. 2A to 2B show the first support leaflet 200a and the second support leaflet 200b in a closed position. By "closed," it is meant that the support leaflets 200 extend across the central opening 101, but not necessarily sized and shaped to completely block the flow of blood through the central opening 101, either together or individually. In comparison, FIG. 2D is a top view looking in the upstream direction of the leaflet support device 10 shown in FIGS. 2A to 2C, except with the first support leaflet 200a and the second support leaflet 200b in an open position. The leaflet first free edge 210a moves apart from the leaflet second free edge 210b to the open position when the pressure of the blood on the inflow side 11 is greater than the pressure on the outflow side 12. This pressure difference also causes the native leaflets to open, causing blood to flow through the central opening 101.

FIGS. 3A to 3D are top views of a support leaflet 200, in accordance with various embodiments. The regions of the support leaflet 200 that are shown in FIGS. 3A to 3D include a leaflet base 204, a leaflet belly 208 terminating at a leaflet free edge 210, and a stiffened region 220 within the leaflet belly 208. The stiffened region 220 is a region of greater stiffness relative to an adjacent region. In the embodiments shown, the stiffened region 220 is made stiff by incorporating reinforcement 225 that is encapsulated between two layers of film forming the support leaflet 200.

Figure 3B:
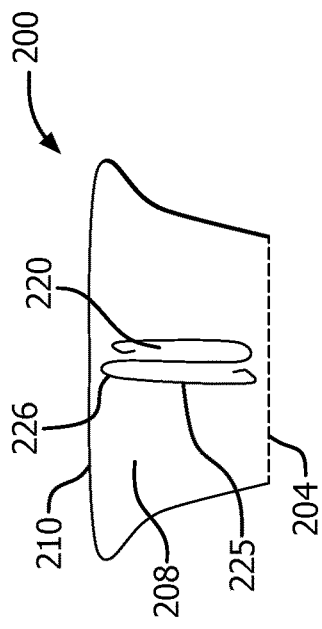
FIGS. 3A to 3D depict leaflet supports with reinforcements in accordance with various embodiments.
Figure 3A:
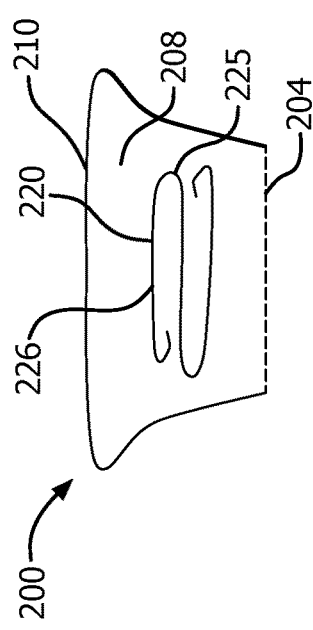
Figure 3D:
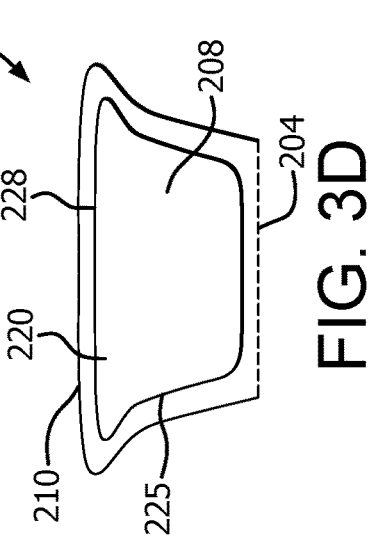
Figure 3E:
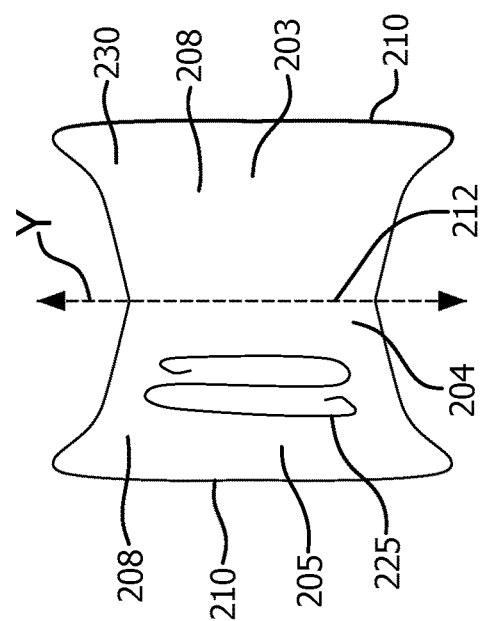
FIG. 3E depicts a deconstructed leaflet support embodiment of FIG. 3A.

FIG. 3E is a top view of a deconstructed support leaflet 200 in accordance with an embodiment shown in FIG. 3A. The regions of the support leaflet 200 that are shown in FIG. 3E include a leaflet base 204, a leaflet belly 208 terminating at a leaflet free edge 210, a stiffened region 220 within the leaflet belly 208, and a frame attachment region 212. In a constructed version of this support leaflet embodiment, the frame attachment region 212 would be disposed around the leaflet attachment region 113 of the frame 100, and the reinforcement 225 would be disposed between a first film layer 203 and a second film layer 205 that are laminated together.

In the embodiment shown, the frame 100 is annular, that is it generally defines a central opening 101 having an axis A-B and has a plurality of undulations 112 that each extend in a direction substantially perpendicular to axis A-B. Stated another way, the plurality of undulations 112 can be substantially co-planar. In some embodiments, the plurality of undulations can extend along a line that forms between a 60° to 90° angle with the A-B axis, e.g., 65°, 70°, 75°, 80°, or 85°. In the embodiment shown, the frame 100 is a wire-like frame.

The annular shape of the frame 100 can be any shape, such as crescent shaped, polygonal (e.g., triangular, rectangular, hexagonal), or rounded (e.g., oval or circle), or semi-rounded (e.g. semi-circular). In the embodiment shown, the frame 100, has a hexagonal shape, with each side of the hexagon bowed inward (e.g., being concave) and each corner being rounded. With this shape, the frame 100 defines a plurality of undulations 112.

The frame 100 is configured to support one or more support leaflets 200. The frame 100 comprises a leaflet attachment region 113 for each support leaflet 200 to be attached. In the embodiment shown, the frame 100 comprises two leaflet attachment regions 113, each leaflet attachment region 113 disposed on opposite sides of frame 100 relative to the other leaflet attachment region 113. The leaflet attachment region 113 defines a leaflet contact surface 114 that is contoured to sufficiently disperse the load on the leaflet base 204 and frame attachment region 212. In addition to load distribution, the leaflet contact surface 114 imparts a shape to the leaflet. In some embodiments, the shape of the leaflet is generally planar when in a closed position and extends across at least a portion of the central opening 101. As such, the leaflet contact surface 114 extends along a plane that is generally transverse to the direction of blood flow, e.g., axis Z shown in FIG. 2C.

The frame 100 is configured to be resiliently compressible in a radial direction such that the frame, when in a compressed state during use, urges against the annulus or the atrium to securely couple the frame to the annulus or the atrium. The shape and size of the frame as well as the material of which the frame is constructed can be varied to obtain the appropriate amount of resilient compressibility. For example, in some embodiments, the frame 100 can comprise a plurality of undulations 112 and can define a closed-shape. In other embodiments, the frame is not a closed shape, e.g., the frame defines an arc or a C-like shape that partially defines the central opening. In addition, the frame 100 can comprise any rigid or semi-rigid biocompatible material. Materials suitable for the frame 100 include, but not limited to, titanium alloys, stainless steel, cobalt-nickel alloy, polypropylene, acetyl homopolymer, acetyl copolymer, other alloys or polymers, or any other material that is generally biocompatible having adequate physical and mechanical properties to function as the frame 100 as described herein. In some embodiments, the frame 100 can be a shape-memory material, such as nitinol, a nickel-titanium alloy.

Frame 110 can comprise other mechanisms to facilitate coupling the frame 110 to the native valve annulus. In some embodiments, the frame comprises one or more tissue anchors configured to engage with the annulus of the atrioventricular valve or with the atrium at the level of or adjacent to the annulus.

The frame 100 can comprise a functional coating or outer layer of material. In some embodiments, the frame 100 can comprise a layer of a secondary material that facilitates support leaflet attachment. For example, the layer can be a coating of a fluoropolymer such as fluorinated ethylene propylene (FEP) to facilitate attachment of a film comprising a fluoropolymer. In some embodiments, the layer can allow for cellular ingrowth, such as by being a porous or non-porous polymer layer.

The frame 100 can be etched, cut, laser cut, stamped, three-dimensional printed, shaped, among other suitable processes, into an annular structure or a sheet of material, with the sheet then formed into an annular structure. The frame shape can be configured for transcatheter or surgical devices.

In accordance with a leaflet support device suitable for surgical implantation, the frame 100 would not need to be resiliently compressible in a radial direction. In lieu of seating the frame in the annulus with a compressible frame, the device can further comprise a sewing cuff about the frame 100 in accordance with embodiments. The sewing cuff is operable to provide structure that receives suture for coupling to the implant site. The sewing cuff may comprise any suitable material, such as, but not limited to, double velour polyester, ePTFE, and silicone. The sewing cuff may be located circumferentially around a perimeter of the base of the frame. The sewing cuff may comprise a filler material, such as, but not limited to, a silicone ring.

Coupled to the frame 100 at the leaflet attachment regions 113 is the first support leaflet 200a and the second support leaflet 200b. The support leaflets 200 are configured to share or distribute the load from an underlying native leaflet in a closed position. In some embodiments, each support leaflet 200 is configured to support at least a portion of an atrial-facing surface of an atrioventricular valve leaflet when in the closed position.

Support leaflets 200 extend radially inward from the frame 100. Each support leaflet 200 defines a frame attachment region 212, a leaflet base 204 extending adjacent the frame attachment region 212 and configured to flex during support leaflet 200 movement, a leaflet belly 208, and a leaflet free edge 210—the leaflet belly 208 terminating at leaflet free edge 210. Each support leaflet 200 can be configured such that the support leaflet 200 pivots about the respective frame attachment region 212 to move between an open and closed position, and each leaflet free edge 210 moves correspondingly with a native leaflet to the open position and moves correspondingly with the native leaflet to the closed position during use.

The support leaflet 200, in accordance with the present disclosure, is configured to couple to the frame 100 by way of the frame attachment region 212. In some embodiments, the frame attachment region 212 is configured to wrap around the leaflet attachment region 113 of frame 100. The frame attachment region 212 can comprise a polymeric adhesive to facilitate coupling the leaflet attachment region to the frame 100. In some embodiments, the support leaflet 200 is a folded film, forming two layers of film laminated together except at the fold (e.g., the frame attachment region 212) where the film is folded around and coupled to the frame 100. This embodiment may be better appreciated with reference to FIG. 3E. The film 230 can be folded in half along axis Y to form support leaflet 200.

In some embodiments, the support leaflets 200 are sized and shaped to correspond to the size and shape of the non-coapting portion of the native leaflet (e.g., the belly of the native leaflet) to be supported. By way of example, in the context of the leaflet support device 10 comprising two support leaflets 200 configured to treat mitral valve prolapse, in some embodiments, the first support leaflet 200a has a larger surface area than the second support leaflet 200b. In addition, in some embodiments, the leaflet first free edge 210a defines a convex line and the leaflet second free edge 210b defines a concave line. With such geometry, the first support leaflet 200a is shaped to correspond to the native anterior leaflet and the second support leaflet 200b for that of the native posterior leaflet.

Being that the support leaflets 200 do not replace a native leaflet but rather support native leaflets, support leaflets 200 need not contact each other or coapt with the opposite native leaflet. As such, each support leaflet 200 comprises an inflow-facing surface 201 and an outflow-facing surface 202, and neither the inflow-facing surface 201 or outflow-facing surface 202 of each support leaflet contact the outflow-facing surface 202 or inflow-facing surface 201, respectively, of an opposite support leaflet 200.

The support leaflet 200 can comprise one or more stiffened regions 220 disposed within the leaflet belly 208, and of a sufficient size and stiffness to support the native leaflet so as to decrease or prevent prolapse of the native leaflet. The stiffened region 220 has a stiffness that is greater than that of the leaflet base 204. In some embodiments, the one or more stiffer regions 220 extend across at least 70% of a dimension of the support leaflet 200 wherein the dimension is substantially transverse to blood flow when in the closed position. In an embodiment, stiffened region 220 is 70% of a dimension of the support leaflet 200 which extends across a sufficient portion of the support leaflet 200 to minimize bending when the support leaflet 200 contacts the limiter 300. In some embodiments, the stiffened region 220 extends along a length that is in the same direction as a line of native leaflet coaptation. In some embodiments, the one or more stiffer regions 220 extend away from the leaflet base 204 (e.g., along a direction that is transverse to the line of native leaflet coaptation).

Figure 3C:
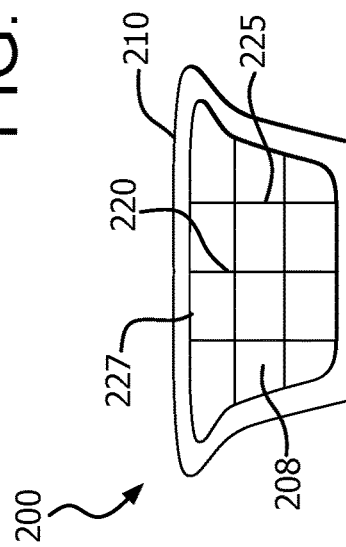

The stiffened region 220 can comprise reinforcement 225 configured to impart a stiffness sufficient to support the native leaflet so as to decrease or prevent prolapse of the native leaflet. In some embodiments, the reinforcement 225 is laminated between two layers of film that form a support leaflet 200. In some embodiments, the reinforcement 225 can be a wire with a serpentine conformation 226, as shown in FIGS. 3A and 3B. In some embodiments, the reinforcement 225 can be a wire that defines an open framework 227, as shown in FIG. 3C. In some embodiments, the reinforcement 225 can be a wire that defines a closed, rounded loop 228, as shown in FIG. 3D. In other embodiments, the reinforcement 225 can be a thickened portion of the support leaflet 200 (e.g., an additional layer of film or piece of material extending across or throughout the region where increased stiffness is desired, such as across or throughout a portion of the leaflet belly 208).

In some embodiments, the support leaflet 200 is configured to couple to the native leaflet. For example, a portion of the support leaflet 200 between the leaflet base 204 and the leaflet free edge 210 can comprise a porous or non-porous polymer configured for cellular ingrowth defining the outflow-facing surface 202. In another option, the support leaflet 200 can comprise anchors configured to couple to the atrial-facing surface of the native leaflet.

The support leaflet 200 can comprise any biocompatible material sufficiently compliant and flexible, such as a biocompatible polymer. In particular, each leaflet base 204 comprises a flexible material that is configured to flex so that the support leaflet 200 moves to the open position as blood begins to flow through the native valve. The support leaflet 200 or the leaflet base 204 can comprise a membrane that is combined with an elastomer to form a composite material. The support leaflet 200 can comprise, according to some embodiments, a composite material comprising an expanded fluoropolymer membrane, which comprises a plurality of spaces within a matrix of fibrils, and an elastomeric material. It should be appreciated that multiple types of membranes and multiple types of elastomeric materials can be combined to form a composite material while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with some embodiments, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, can comprise PTFE homopolymer. In alternative embodiments, blends of PTFE, expandable modified PTFE and/or expanded copolymers of PTFE can be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure, such as a structure incorporating pores, for achieving the desired leaflet performance. Other biocompatible polymers which can be suitable for use in leaflet include but are not limited to the groups of urethanes, silicones (organopolysiloxanes), copolymers of silicon-urethane, styrene/isobutylene copolymers, polyisobutylene, polyethylene copoly(vinyl acetate), polyester copolymers, nylon copolymers, fluorinated hydrocarbon polymers and copolymers or mixtures of each of the foregoing.

In some embodiments, support leaflet construct materials include: a fluoropolymer membrane layer or a laminate having more than one fluoropolymer membrane layer, and/or a composite material having at least one fluoropolymer membrane layer having a plurality of pores and an elastomer present in the pores of at least one of the fluoropolymer membrane layers. In some embodiments, at least one fluoropolymer membrane layer is an expanded fluoropolymer membrane layer, such as ePTFE. In some embodiments, an elastomer is contained within the expanded fluoropolymer membrane layer. In some embodiments, the elastomer comprises a silicon, a urethane, or a fluoroelastomer, such as, a copolymer of perfluoromethyl vinyl ether and tetrafluoroethylene or (per)fluoroalkylvinylethers (PAVE). In some embodiments, the composite material comprises fluoropolymer membrane by weight in a range of about 10% to 90%. In some embodiments, the TFE/PMVE copolymer comprises between about 40 and 80 weight percent perfluoromethyl vinyl ether and complementally 60 and 20 weight percent tetrafluoroethylene.

The limiter 300 is a component or a plurality of components that are configured to limit the degree of movement of at least one of the one or more support leaflets 200 when the one or more support leaflets 200 are moving from the open to the closed position. Each support leaflet 200 together with the one or more limiters 300 is configured to restrict the movement of the native leaflet so as to decrease or prevent prolapse of the native leaflet, such as an atrioventricular valve leaflet. In the embodiment shown in FIGS. 2A, 2B, and 2C, the limiter 300 comprises a bridge 310 and a plurality of tethers 320.

The bridge 310 is configured to support the load of the tethers 320, thereby resisting movement of at least one support leaflet 200. The bridge 310 extends across the central opening 101 of the frame 100. In the embodiment shown, an intermediate portion 315 of the bridge 310 is spaced apart from the central opening 111 defined by the frame 100. For example, the bridge 310 comprises a first bridge post 313, a second bridge post 312, and a crossbar 314 that extends therebetween. The first bridge post 313 and the second bridge post 312 are each coupled to the frame 100 at sites that are spaced apart from each other and extend away from the central opening 111. In some embodiments, the first bridge post 313 and the second bridge post 312 would extend between the native leaflets and toward the ventricle during use. In the embodiment shown, the first bridge post 313 is coupled to the frame 100 opposite from where the second bridge post 312 is coupled to the frame 100. In some embodiments, the bridge 310 and particularly, crossbar 314, comprises a cross-sectional profile that would reduce the impact on the blood or the flow of blood, such as an elliptical profile oriented so that the major axis is substantially aligned with the direction of blood flow.

Like the frame 100, the bridge 310 can also have a wire structure. The bridge 310 can be composed of materials that are also suitable for the frame 100 and can include, but are not limited to, titanium alloys, stainless steel, cobalt-nickel alloy, polypropylene, acetyl homopolymer, acetyl copolymer, other alloys or polymers, or any other material that is generally biocompatible having adequate physical and mechanical properties to function as the bridge 310 as described herein. In some embodiments, the bridge 310 can be a shape-memory material, such as nitinol, a nickel-titanium alloy.

The limiter 300 further comprises one or more tethers 320. Tether 320 can be a thread that is generally inelastic along the length of the thread but can withstand repetitive tensioning and bending. For example, in some embodiments, the tether 320 comprises an ePTFE material. Each tether 320 is coupled to the bridge and to at least one of the one or more support leaflets 200. Much like the reinforcement 225, a tether portion 321 can be laminated between layers of film that form the support leaflet 200. An intermediate section 322 of the tether 320 can extend from the leaflet free edge 210. The length of the tether 320 between the leaflet free edge 210 and the bridge 310 determines the degrees of excursion of the support leaflet 200.

Figure 4A:
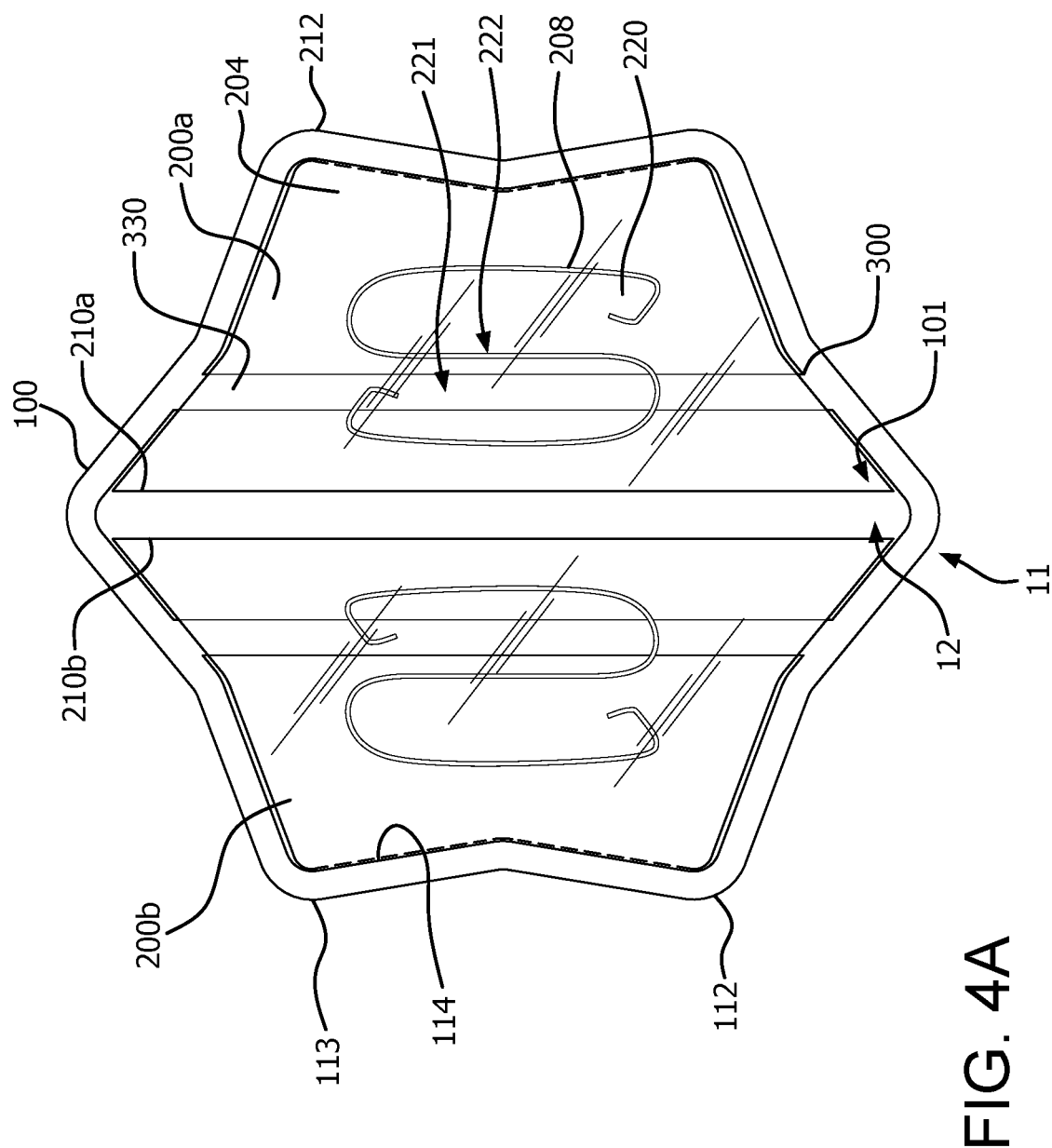
FIG. 4A is an outflow side, top view of a leaflet support device in accordance with an embodiment, where the support leaflets are in a closed position.
Figure 4B:
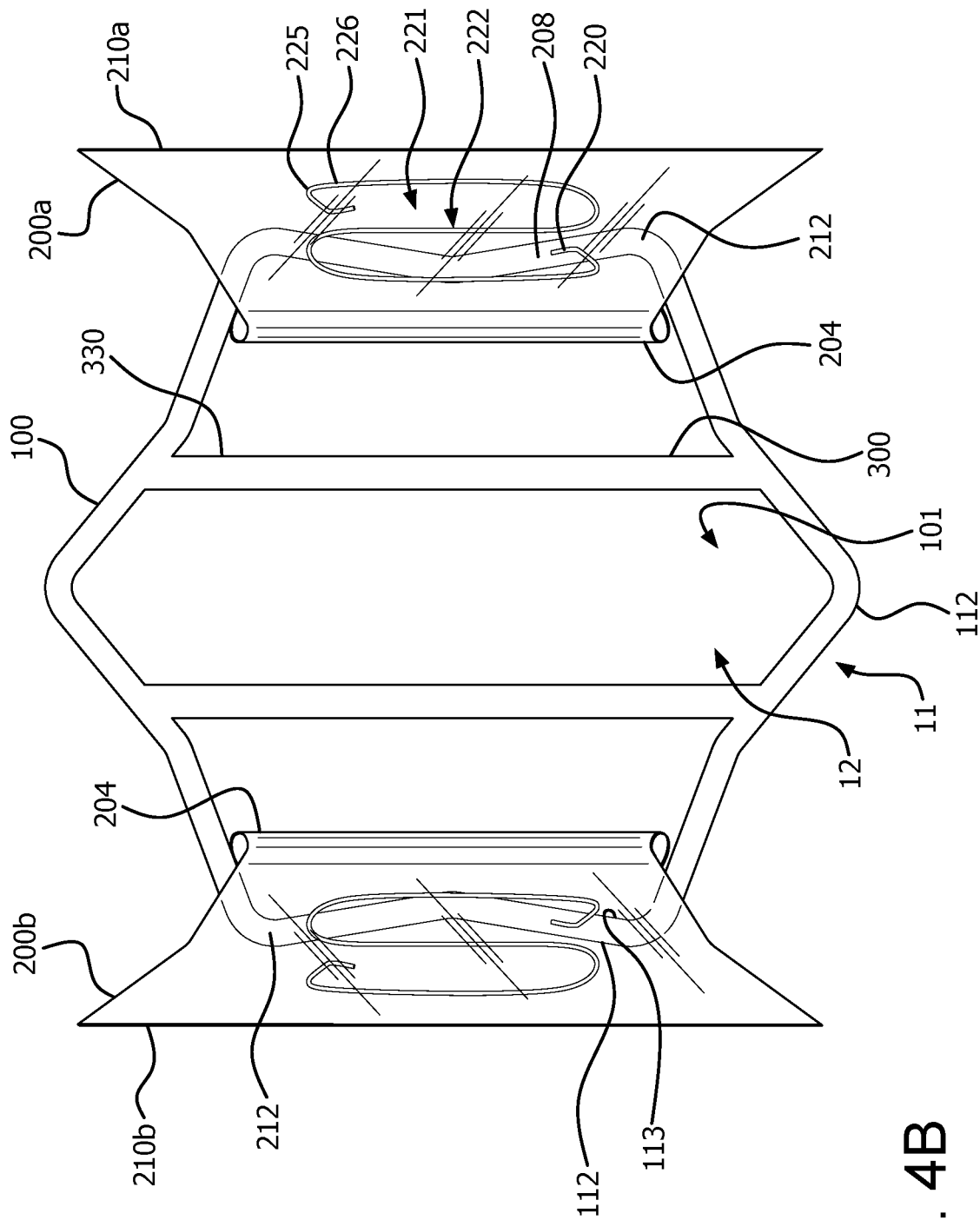
FIG. 4B is an outflow side, top view of the leaflet support device of FIG. 4A, except with the leaflet supports in an open position.

FIGS. 4A to 4B are a top, outflow side views of a leaflet support device 10, in accordance with another embodiment. The leaflet support device embodiment shown in FIGS. 4A to 4B is the same as the embodiment shown in FIGS. 2A to 2D, except the limiter 300 is different. The components of the leaflet support device 10 that are visible in FIGS. 4A to 4B include a frame 100, a first support leaflet 200a, a second support leaflet 200b, and two limiters 300, each limiter 300 being a bridge 330.

The bridge 330 is configured to resist movement of at least one support leaflet 200 through contact with the support leaflet 200 when in the closed position on the inflow-facing surface 201, which is opposite from the outflow-facing surface 202 visible in FIG. 2A. For example, the bridge 330 extends across the central opening 101 of the frame 100 to limit the degree of excursion of the one or more support leaflets 200.

The bridge 330 can contact the support leaflet 200 along a number of locations. In some embodiments, the bridge 330 contacts the support leaflet 200 along an intermediate portion 221 (e.g., a central portion 222) of the stiffened region 220. In some embodiments, the bridge 330 extends along a length that is in the same direction as a line of native leaflet coaptation. To mitigate the impact on blood flow, in some embodiments, the bridge 330 is closer to the leaflet base 204 than to the corresponding leaflet free edge 210.

Like the frame 100, the bridge 330 can also have a straight wire-like structure. In some embodiments, the bridge 330 comprises a cross-sectional profile to reduce the impact on the blood or the flow of blood, such as an elliptical profile. The bridge 330 can be composed of materials that are also suitable for the frame 100 and can include, but are not limited to, titanium alloys, stainless steel, cobalt-nickel alloy, polypropylene, acetyl homopolymer, acetyl copolymer, other alloys or polymers, or any other material that is generally biocompatible having adequate physical and mechanical properties to function as the bridge 330 as described herein. The bridge 330 can also be comprised of a polymeric material that is generally inelastic along its length and having adequate physical and mechanical properties to function as the bridge 330 as described herein. In some embodiments, the bridge 330 can be a shape-memory material, such as nitinol, a nickel-titanium alloy.

In some embodiments the leaflet support can be collapsed and delivered through the patient's vasculature via a catheter.

Figure 12:
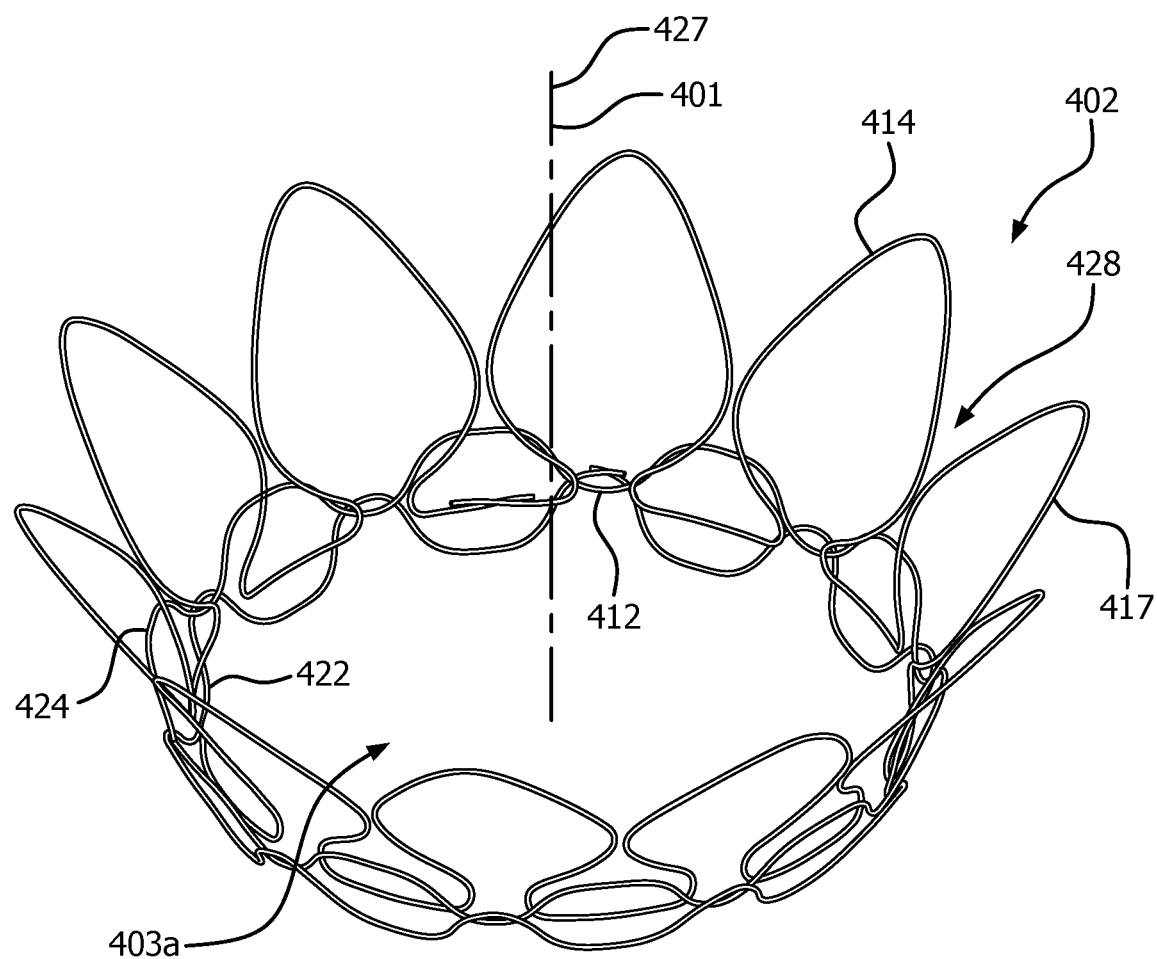
FIG. 12 is a perspective view of a frame for a leaflet support device, in accordance with an embodiment.

In accordance with another embodiment, a leaflet support device comprises a frame and one or more support leaflets. FIG. 12 is a perspective view of a frame 402. The frame 402 defines a shape defined by a tubular member 404 bisected by a flat ring 428 at a base 412 of the tubular member 404. The tubular member 404 defines a tubular member central axis 401 and has a decreasing taper from a first end 414 to the base 412 and defines a tubular member central opening 403a at the base 412 through which blood flows during use. The tubular member 404 is configured to conform to and be coupled with an atrial side of a heart adjacent to an atrioventricular valve. The flat ring 428 defining a ring central axis 427 has a second frame central opening 403 through which blood flows during use. The flat ring 428 is substantially perpendicular to and coaxial with the tubular member central axis 401. The flat ring 428 defines an inner portion 422 that extends into the tubular member central opening 403a and an outer portion 424 that extends away from the tubular member central opening 403a. The outer portion 424 is configured to rest against a ventricular side of an annulus of the atrioventricular valve.

Figure 15:
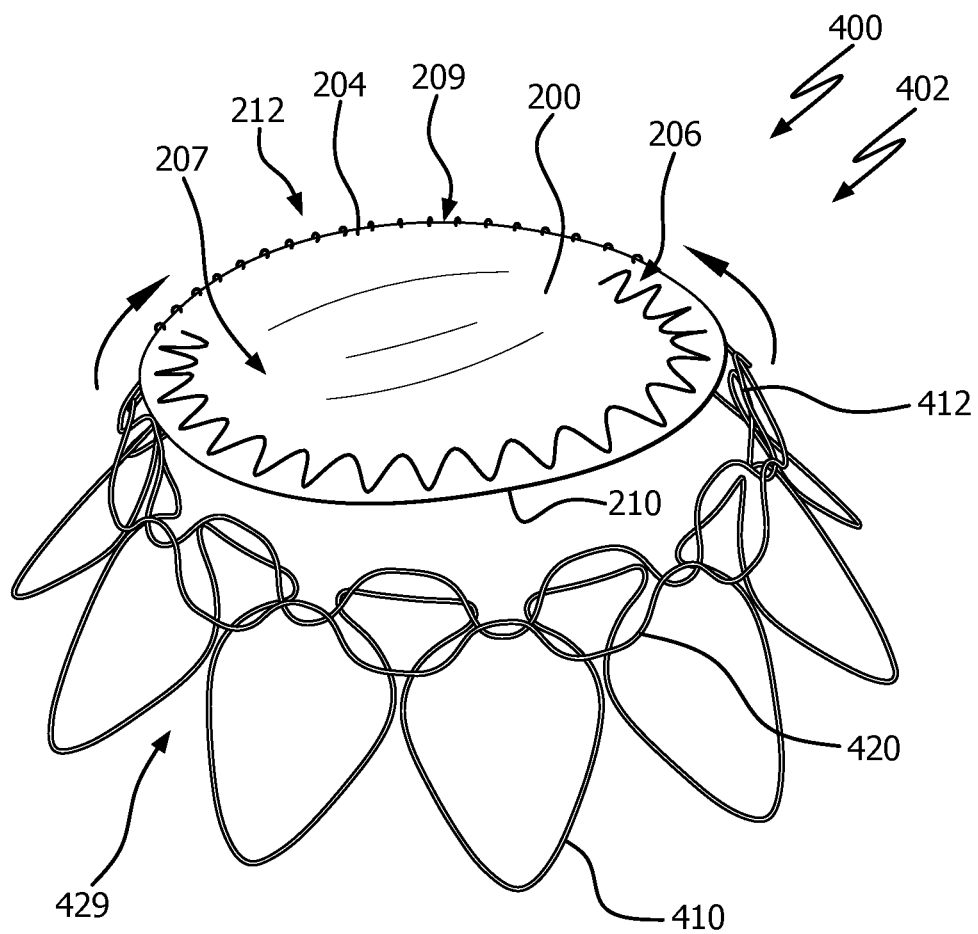
FIG. 15 is a perspective view of a leaflet support device including a first frame, a second frame, and a leaflet support, in accordance with an embodiment.

Each of the one or more support leaflets 200 comprise a leaflet attachment region 209 either coupled to the flat ring 428 or coupled to the base 412 adjacent the flat ring 428 and a leaflet free edge 210 opposite the leaflet attachment region 209, as shown in perspective view in FIG. 15. Each support leaflet 200 is configured to pivot about the respective leaflet attachment region 209 to move between an open and a closed position. When in the closed position, the support leaflet 200 lies adjacent a ventricular side 429 of the second frame 420. Each support leaflet 200 is configured to support at least a portion of an atrial-facing surface of an atrioventricular valve leaflet when in the closed position. The inner portion 422 of the second frame 420 is configured to limit the degree of movement of at least one of the one or more support leaflets 200 when the one or more support leaflets 200 are moving from the open to the closed position, wherein the support leaflet coapts against the ventricular side 429 of the inner portion 422 of the second frame 420. Each support leaflet 200 is configured such that the leaflet free edge 210 moves correspondingly with an atrioventricular valve leaflet to the open position and moves correspondingly with the atrioventricular valve leaflet to the closed position during use.

In accordance with another embodiment, the frame 402 described above comprises a first frame 410 defining the tubular member 404 and a second frame 420 defining the flat ring 428. The second frame 420 is coupled to the first frame 410 at the base 412 and substantially perpendicular to and coaxial with the first frame central axis 411.

In an embodiment where there are two support leaflets 200, the first support leaflet 200a comprises a first frame attachment region 212a coupled to the flat ring 428 or coupled to the base 412 adjacent the flat ring 428 and a leaflet first free edge 210*a* opposite the first frame attachment region 212*a*. The second support leaflet 200*b* comprises a second frame attachment region 212*b* coupled to the frame 402 opposite from where the first frame attachment region 212*a* is coupled and a leaflet second free edge 210*b* opposite the second frame attachment region 212*b*.

In other embodiments, each support leaflet 200 is sized such that the first support leaflet 200*a* and the second support leaflet 200*b* do not overlap with each other when in the closed position.

In other embodiments, the first support leaflet 200*a* has a larger surface area than the second support leaflet 200*b*.

In other embodiments, each support leaflet 200 has a size suitable to cover at least half of a non-coapting portion of the atrial-facing surface of the respective atrioventricular valve leaflet, when the valve leaflet is in the closed position.

In other embodiments, the leaflet first free edge 210*a* defines a convex line and the second free edge defines a concave line.

In other embodiments, a portion of the support leaflet 200 between the leaflet attachment region 209 and the leaflet free edge 210 comprises a porous or non-porous polymer configured for cellular ingrowth and defining at least a portion of a ventricular-facing surface.

In other embodiments, each support leaflet 200 comprises one or more stiffer regions 220 with a stiffness that is greater than an adjacent region 207. In an embodiment, the one or more stiffer regions 220 with greater stiffness extend across at least 70% of a dimension of the support leaflet 200 wherein the dimension is substantially transverse to blood flow. In an embodiment, the one or more stiffer regions 220 with greater stiffness extends along a length that is in the same direction as a line defined by native leaflet coaptation. In an embodiment, each support leaflet 200 comprises one or more stiffer regions 220 with a stiffness that is greater than an adjacent region 207 and wherein at least a portion of the one or more stiffer regions 220 with a stiffness that is greater than an adjacent region 207 is configured to abut with the inner portion 422 of the flat ring 428.

In other embodiments, the tubular member 404 or the first frame 410 define a plurality of petals or loops 417 which extend at an angle from the tubular member 404 or first frame central axis 411, respectively, defining the tubular shape having the decreasing taper.

In other embodiments, the frame 402 or the first frame 410 and second frame 420 are configured to be resiliently compressible in a radial direction such that the frame 402, when in a compressed state during use, urges against the annulus or the atrium to couple the frame 402 or the first frame 410 and second frame 420 to the annulus 452 and/or the atrium 254.

In other embodiments, the frame 402 or either or both of the first frame 410 and second frame 420 comprises one or more tissue anchors configured to engage with the annulus of the atrioventricular valve or with the atrium at the level of or adjacent to the annulus.

In other embodiments, the support leaflet 200 comprises anchors configured to couple to an atrial-facing surface of an atrioventricular valve leaflet.

In other embodiments, the support leaflet 200 is configured to be tethered to a ventricular structure. In accordance with another embodiment, the leaflet support device 400 further comprised a tether 430 coupled to the support leaflet 200 that is configured to be coupled to a ventricular structure. In accordance with an embodiment, the tether is suture, fiber, or the like.

Figure 13:
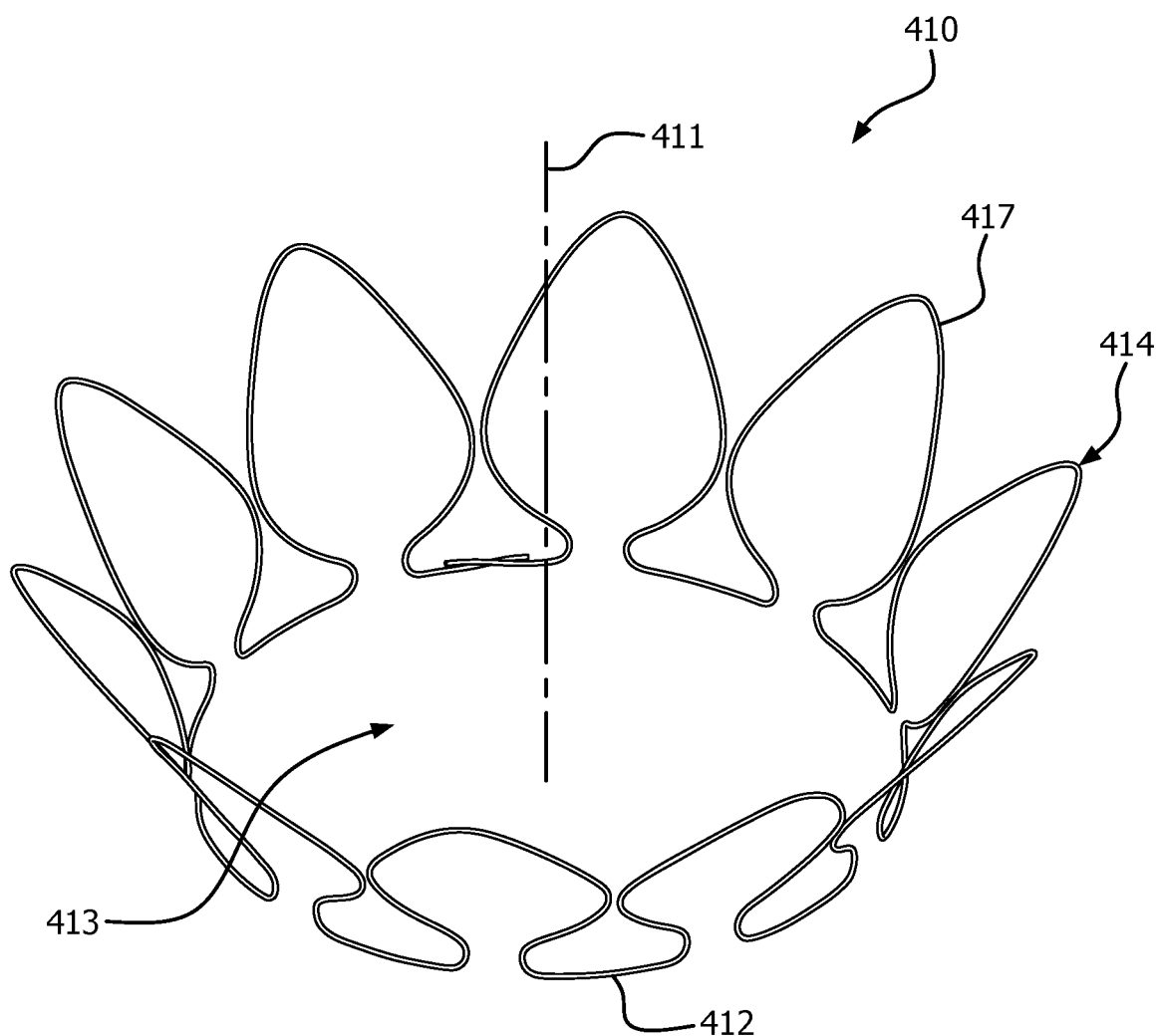
FIG. 13 is a perspective view of a first frame, in accordance with an embodiment.

In other embodiments, the leaflet support device 400 comprises a first frame 410, a second frame 420 and one or more support leaflets 200, as shown in perspective view in FIG. 15. FIG. 13 is a perspective view of a first frame 410, in accordance with an embodiment. The first frame 410 defines a tubular shape defining a first frame central axis 411 and having a decreasing taper from a first end 414 to a base 412 and defining a first frame central opening 413 at the base 412 through which blood flows during use. The first frame 410 is configured to conform to and be coupled with an atrial side of a heart adjacent to an atrioventricular valve.

Figure 14:
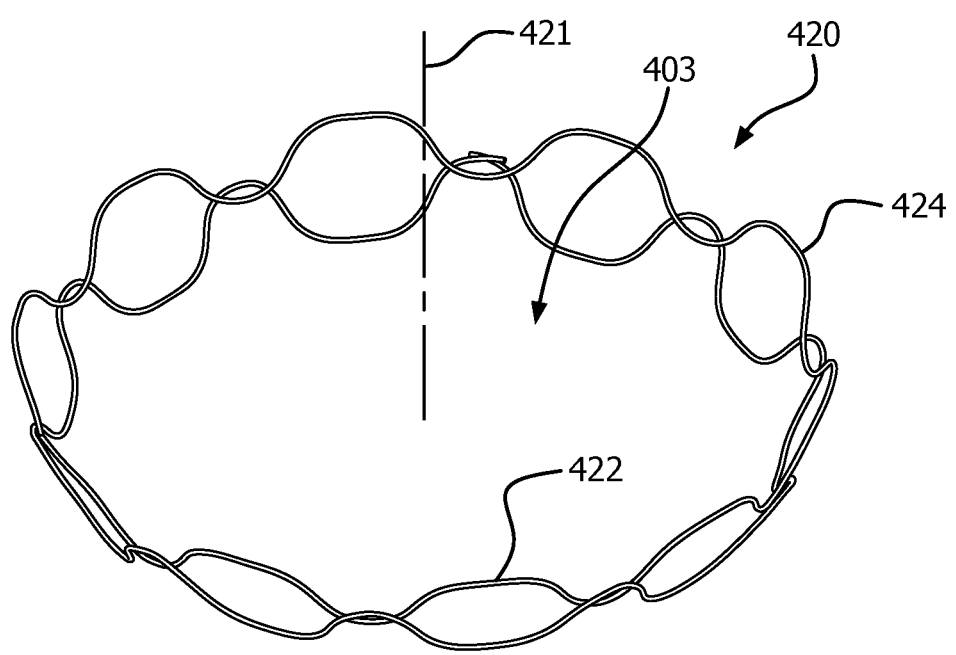
FIG. 14 is a perspective view of a second frame, in accordance with an embodiment.

FIG. 14 is a perspective view of a second frame 420, in accordance with an embodiment. The second frame 420 defines a flat ring shape defining a second frame central axis 421 having a second frame central opening 403 through which blood flows during use. The second frame 420 is coupled to the first frame 410 at the base 412 and substantially perpendicular to and coaxial with the first frame central axis 411. The second frame 420 defines an inner portion 422 that extends into the first frame central opening 413 and an outer portion 424 that extends away from the first frame central opening 413. The outer portion 424 is configured to rest against an upstream side of an annulus of the atrioventricular valve. Each support leaflet 200 comprises a leaflet attachment region 209 coupled to the base 412 of the first frame 410 and a leaflet free edge 210 opposite the leaflet attachment region 209. Each support leaflet 200 is configured to pivot about the respective leaflet attachment region 209 to move between an open and a closed position. While in the closed position the support leaflet 200 lies adjacent a ventricular side 429 of the second frame 420, wherein each support leaflet 200 is configured to support at least a portion of an atrial-facing surface of an atrioventricular valve leaflet when in the closed position. The inner portion 422 of the second frame 420 is configured to limit the degree of movement of at least one of the one or more support leaflets 200 when the one or more support leaflets 200 are moving from the open to the closed position, wherein each support leaflet 200 coapts against the ventricular side 429 of the inner portion 422 of the second frame 420. Each support leaflet 200 is configured such that the leaflet free edge 210 moves correspondingly with an atrioventricular valve leaflet to the open position and moves correspondingly with the atrioventricular valve leaflet to the closed position during use.

Figure 16A:
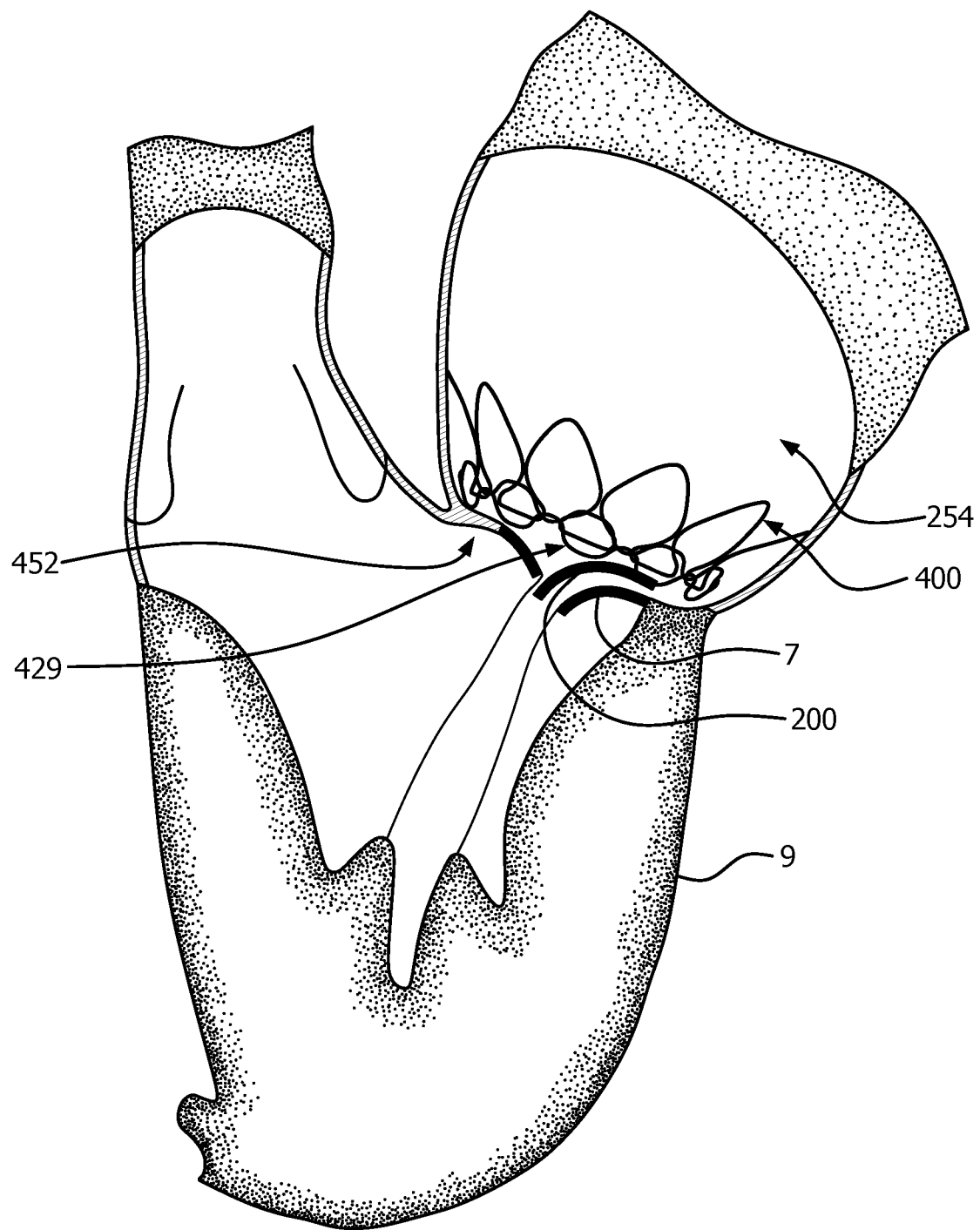
FIG. 16A is a cutaway view of an embodiment of a leaflet support device in a heart having leaflets coapting the support leaflet, in accordance with an embodiment.
Figure 16B:
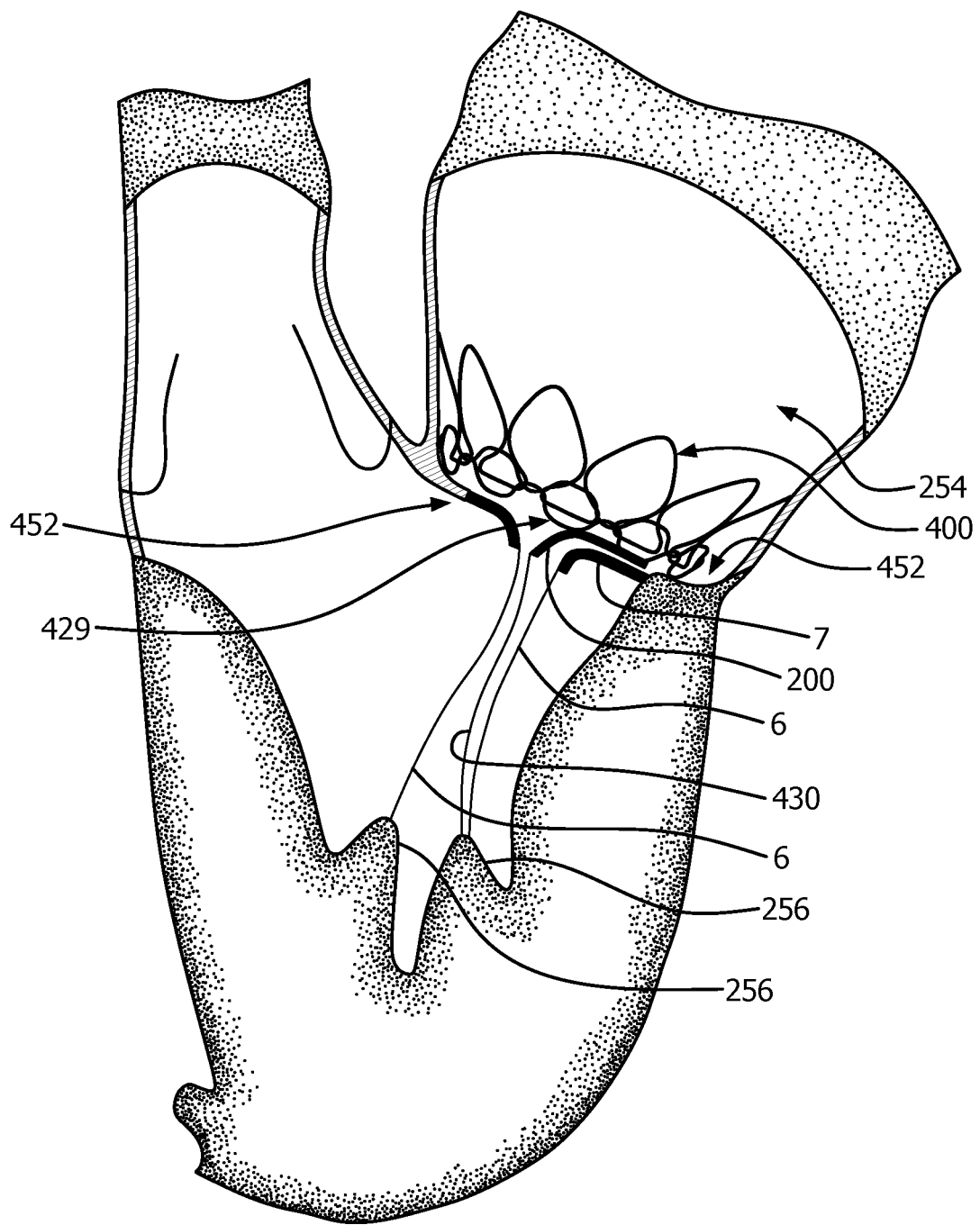
FIG. 16B is a cutaway view of an embodiment of a leaflet support device in a heart having non-coapting leaflets wherein the leaflet support includes a tether coupled to a papillary muscle, in accordance with an embodiment.

FIG. 16A is a cutaway view of an embodiment of a leaflet support device 400 in a heart 9 having leaflets 7 coapting the support leaflet 200, in accordance with an embodiment. The leaflet support device 400 engages the annulus 452 and the atrium 254. FIG. 16B is a cutaway view of an embodiment of a leaflet support device 400 in a heart 9 wherein the support leaflet 200 includes a tether 430 coupled to a papillary muscle 256, in accordance with an embodiment.

A method of delivering the leaflet support device via a catheter can comprise providing a delivery catheter having an expandable leaflet support device in a collapsed state constrained over or within the delivery catheter at a distal end of the delivery catheter; passing the delivery catheter through the introducer sheath and into valve annulus; positioning the distal end of the delivery catheter so that the leaflet support device is properly positioned and oriented within the valve annulus; and expanding the leaflet support device at the valve annulus into contact therewith.

A method of making a leaflet support device, in accordance various embodiments can comprise providing a frame 100 with a bridge 310 (FIG. 2A) or a bridge 330 (FIG. 4A) coupled thereto in accordance with the present disclosure;

folding a leaflet support material around the frame 100 such that the frame is disposed in a fold of the leaflet support material and the support leaflet will comprise a first layer of film and a second layer of film; placing a reinforcement 225 between the first layer and second layer of film; and laminating the first layer and the second layer together to form the support leaflet. In some embodiments, the method can further comprise placing a tether portion 321 between the first layer and the second layer such that the tether 320 exits the leaflet free edge 210 and coupling the tether 320 to the bridge 310.

Having generally described this disclosure, a further understanding can be obtained by reference to certain specific examples illustrated below which are provided for purposes of illustration only and are not intended to be all inclusive or limiting unless otherwise specified.

Example 1

A mitral leaflet support device was constructed as follows.

Figure 5:
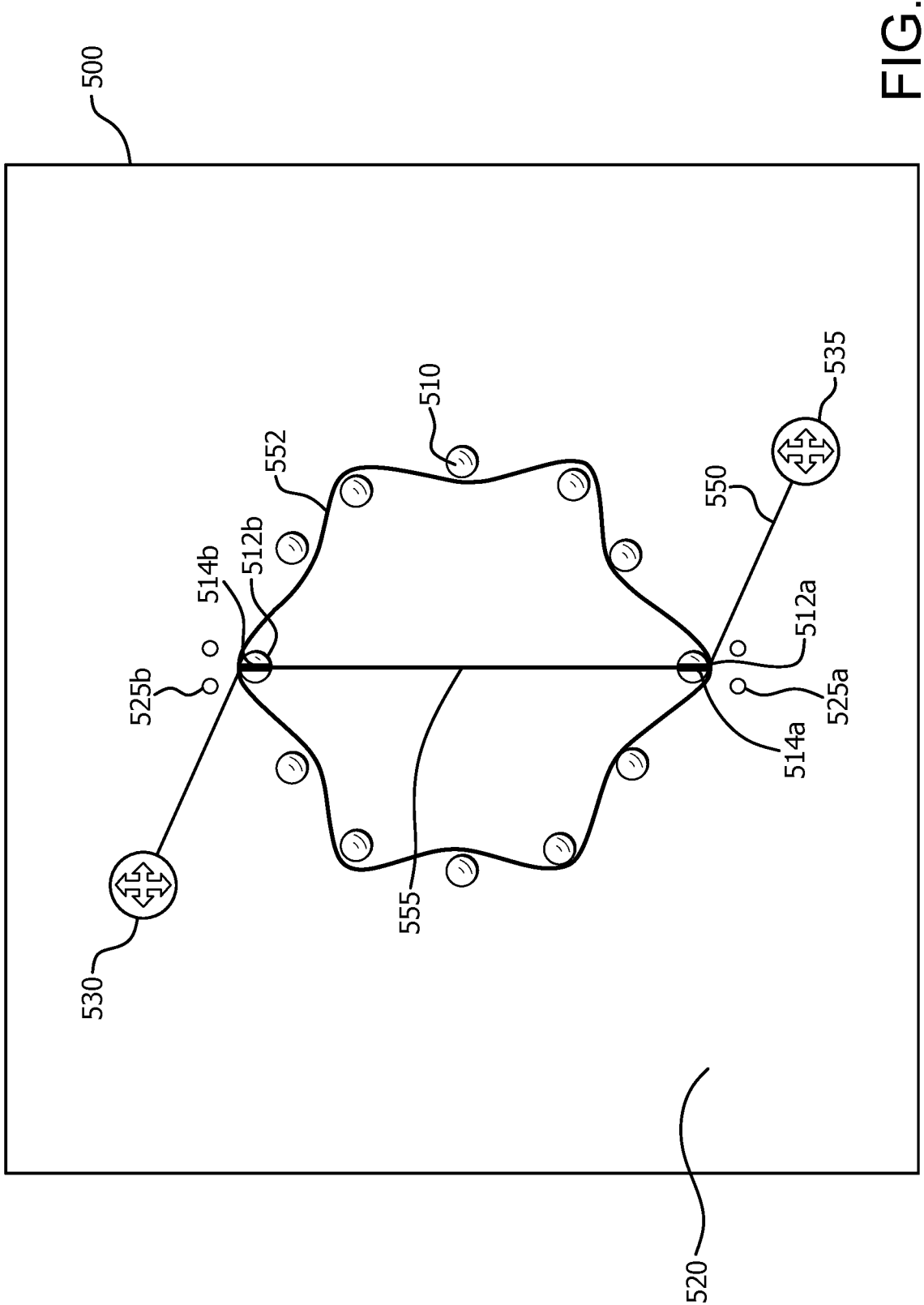
FIG. 5 is a top view of a schematic of a frame-shaping pin jig with a wire interlaced in the pins as further described in the Examples.

Frame and Bridge: A frame-shaping pin jig 500 as shown in FIG. 5 was constructed having the following features: (i) twelve of fourteen 3.175 mm diameter stainless steel roll pins 510 project upward from an aluminum base plate 520 and were arranged generally to define a circle with a 25 mm diameter with spacing between neighboring roll pins 510 being generally the same, (ii) the other two of the fourteen roll pins 510 were elevated pins, projecting upward approximately 10 mm further than the other twelve and were disposed within the above-described circle of pins 510 as illustrated (referred to as the first elevated pin 512a and the second elevated pin 512b), and (iii) two rotatable screws project upward from the aluminum base plate 520, namely a first screw 530 and a second screw 535 at opposite corners of the base plate 520. The first elevated pin 512a and the second elevated pin 512b each had a notch (referred to as the first notch 514a and the second notch 514b) at the top. The base plate had four holes, namely, a first pair of lock wire holes 525a and a second pair of holes 525b, adjacent to the base of the respective elevated pin, 512a and 512b. Nitinol wire (Fort Wayne Metals, Fort Wayne IN, nominal diameter 0.322 mm) was obtained, electropolished to a diameter of 0.317 mm, and heat treated in air to obtain a straight configuration. The nitinol wire was wound around the pins 510. Starting at one of the elevated pins with the wire end locked under the first screw 530, the wire 550 was wrapped entirely around (360 degrees counterclockwise) the collection pins 510 in an interlacing manner to form a serpentine pattern. The wrapping was continued in the same manner for another 180 degrees counterclockwise. The wire 550 was bent at the base of a first elevated pin 512a, extended up the length of the first elevated pin 512a, bent and extended from the first notch 514a to the second notch 514b in the top of the opposing second elevated pin 512b, and bent, extending to the base of the second elevated pin 512b, thus forming a bridge pass 555 with wire 550. The interlaced wrapping was resumed in the clockwise direction for 180 degrees thereby completing another full pass around the pins 510. The wrapping was continued in the same manner for another 360 degrees clockwise. Another bridge pass 555 was formed by crossing the first elevated pin 512a and the second elevated pin 512b as described above and the interlaced wrapping was resumed for 180 degrees in the counterclockwise direction. Yet another bridge pass 555 was formed between the first elevated pin 512a and the second elevated pin 512b and the interlaced wrapping was resumed in the clockwise direction for 180 degrees. Wire wrapping was continued by forming another bridge pass 555 as described above, wrapping 180 degrees in the counterclockwise direction, forming another bridge pass 555, and wrapping in the clockwise direction for 540 degrees. The end of the wire was then locked under the second screw 535.

The wire bundle 552 of wire 550 adjacent the first elevated pin 512a and the second elevated pin 512b was secured to the frame-shaping pin jig 50 by extending stainless steel wire (Stainless steel safety lock wire, 0.5 mm diameter, specifications: MS20995C20E, MIL-W-6713, QQW423B) around the elevated pin 512a, over the wire bundle 552, and through each of the pair of lock wire holes 525a. The lock wire was secured on the back of the base plate 520 by twisting the ends of the lock wire together. The wire bundle 552 adjacent to the second elevated pin 512b was secured in a similar manner.

Figure 6:
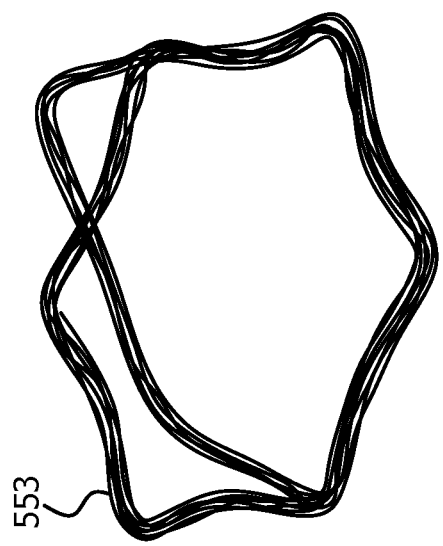
FIG. 6 is a top, perspective view of a shaped bundle of wire formed from a frame-shaping pin jig like that illustrated in FIG. 5.

The frame-shaping pin jig 500 with the wire bundle 552 was placed in a forced air oven set to 450° C. for 20 min. After heating, the assembly was quenched in water at ambient temperature and the wire bundle 552 was removed from the frame-shaping pin jig 500. The ends of the wire were trimmed to form the shaped bundle 553, as shown in FIG. 6. Next, FEP powder (Daikin America, Orangeburg N.Y.) was then applied to the shaped bundle 553. More specifically, the FEP powder was stirred to form an airborne "cloud" in an enclosed blender, while the wire assembly was suspended in the cloud. The shaped bundle 553 was removed and momentarily placed in a forced air oven set to 320° C. in order to bond the powder to the shaped bundle 553.

Figure 7:
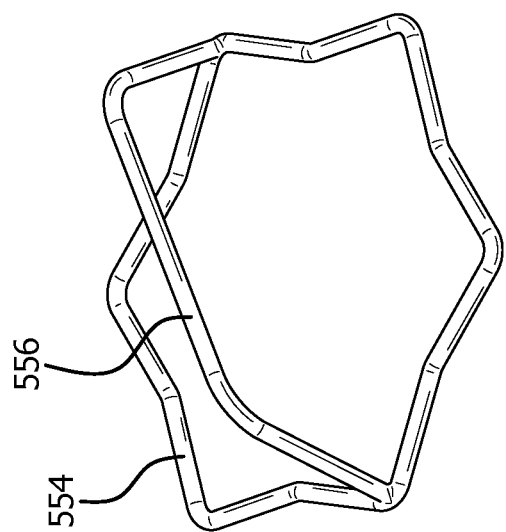
FIG. 7 is a top, perspective view of a frame that was formed from the shaped bundle of wire shown in FIG. 6.

Next, an FEP-ePTFE composite film having the following properties was obtained: thickness of 0.04 mm; width of 6 mm; a maximum tensile force per width in the longitudinal direction of 4.4 N/mm [11.48 kg/in]. The maximum tensile force per width was measured with a cross head speed of 200 mm/min and a grip distance of 25.4 mm. The shaped bundle 553 after coating with FEP was helically-wrapped with the composite film. The film-wrapped bundle was placed in a forced air oven set to 280° C. for 10 min. The resulting frame 554 is shown in FIG. 7, depicting a bridge 556 formed with the five bridge passes wrapped with the film.

Figure 8:
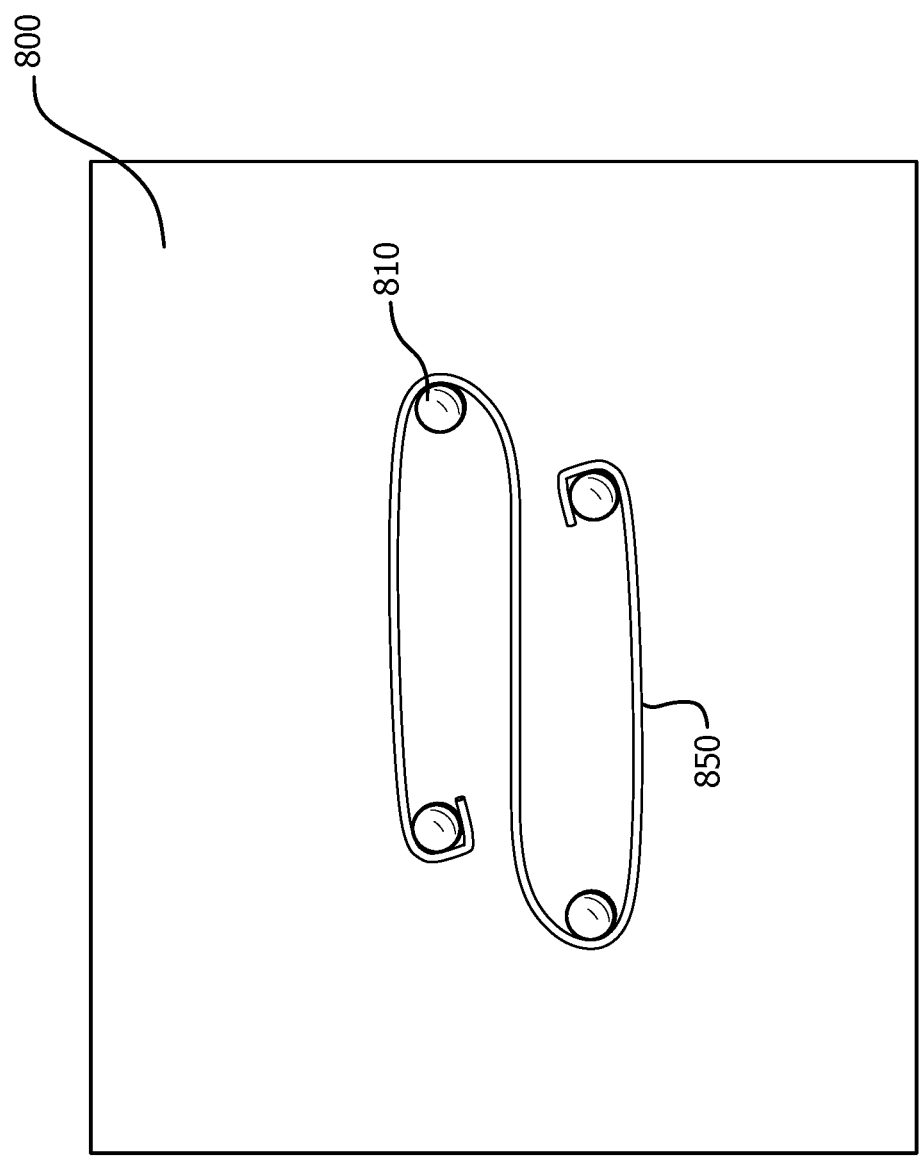
FIG. 8 is a top view of a schematic of a reinforcement shaping jig with a wire wrapped around the pins as further described in the Examples.

Reinforcement: As shown in FIG. 8, a reinforcement 850 in an S-shape conformation with rounded ends was constructed by wrapping a nitinol wire around pins 810 arranged in a 4-point, rectangular pattern on a jig 800. The same type of nitinol wire used to make wire bundle 552 was used to make reinforcement 850. The S-shaped reinforcement 850 was heat treated in a forced air oven set to 450° C. for 10 min. This process was repeated to make a total of two reinforcements.

Figure 9A:
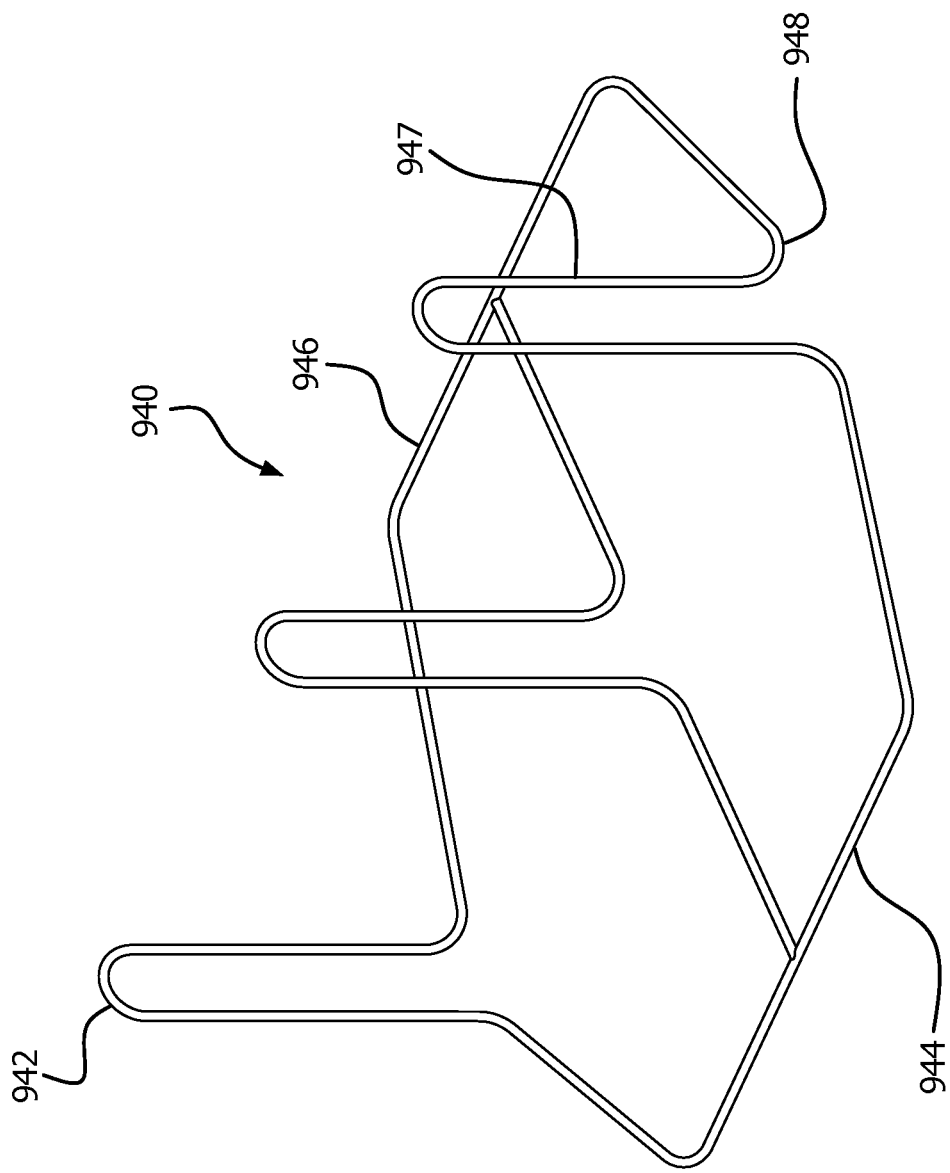
FIG. 9A is a top perspective view of a shaped fiber formed with the shaping tool shown in FIG. 9B as further described in the Examples.
Figure 9B:
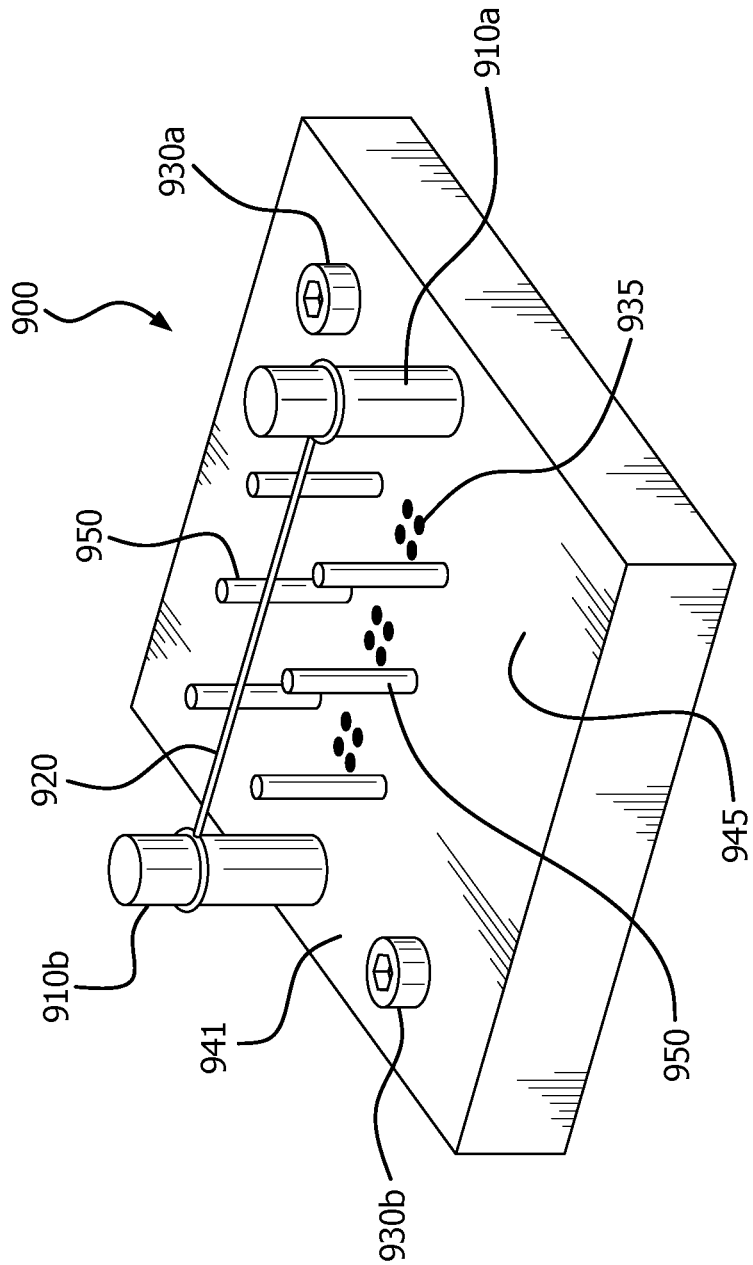
FIG. 9B is a top perspective view of a schematic of a fiber shaping tool as further described in the Examples.

Tether: To form a shaped fiber 940 tether component as shown in FIG. 9A, an ePTFE fiber (RASTEX® 2400 denier ePTFE sewing thread, part number S024T2, W.L. Gore & Associates, Inc., Elkton, MD) was obtained. The fiber was wrapped on the fiber shaping tool 900 shown in FIG. 9B. The fiber shaping tool 900 included an aluminum plate 941 from which two tall posts 910a, 910b extended upward from a surface 945 of the plate. The tool 900 also comprised a suspension wire 920 extending between the two tall posts 910a, 910b, and two lock screws 930a, 930b, each being adjacent yet spaced apart from a different tall post 910a, 910b. Flanking the suspension wire 920 on each side is two rows of three short pins 950 parallel to the suspension wire. The suspension wire 920 was parallel to the surface 945 of the aluminum plate 941 at a height above the plate equal to the height of the elevated pins 512a and 512b on the frame-shaping pin jig 500. Starting at one of the two lock screws 930a, 930b the fiber 940 was wrapped around the short pins 950 and over the suspension wire 920 to form the shape in FIG. 9A. The bases 948 of the vertical portions 947 of the fiber 940 (shown in FIG. 9A) were held adjacent the aluminum plate 941 with a stainless steel lock wire that extended through the lock wire holes 935 and was secured on the back of the plate 941. The shape of the fiber 940 was set by heating the fiber on the shaped fiber shaping tool 900 for about 10 min in a forced air oven at 260° C. The shaped fiber 940 was then removed from the fiber shaping tool 900, and trimmed.

Leaflet Support Material: A second ePTFE composite film was obtained. The second composite film comprised ePTFE film and a fluoroelastomer. Expanded PTFE film was manufactured according to the general teachings described in U.S. Pat. No. 7,306,729. The amorphously locked ePTFE membrane was tested in accordance with the methods described herein. The ePTFE membrane had a mass per area of about 0.5 g/m$^2$, a matrix tensile strength of about 670 MPa in the longitudinal direction and about 350 MPa in the transverse direction. This membrane was imbibed with a copolymer fluoroelastomer. The fluoroelastomer was formulated according to the general teachings described in U.S. Pat. No. 7,462,675. The copolymer consists essentially of between about 65 and 70 weight percent perfluorom ethyl vinyl ether and complementally about 35 and 30 weight percent tetrafluoroethylene. The fluoroelastomer was dissolved in Fluorinert Electronic Liquid FC-72 (3M, St Paul, MN) in a 1.5% concentration. The solution was coated onto a polyolefin backer film and the ePTFE membrane was laminated to the coating solution. The resulting package was dried in a convection oven set to 110° C. for 45 seconds. The resulting composite material had a mass per area of 1.5 g/m$^2$.

Thirty layers of the above-described second composite material were circumferentially wrapped around a 2.54 cm diameter, 15 cm stainless steel mandrel that was covered with KAPTON polyimide film (Type 200HN. E. I. DuPont de Nemours & Co., Wilmington, DE). This assembly was placed in a forced air oven set to 280° C. for 30 min. The assembly was removed from the oven and allowed to cool. The resulting cylinder of material was slit longitudinally to form a coupon of the support leaflet material that was approximately 8 cm by 8 cm. The coupon was removed from the mandrel.

Assembly of Components: The coupon of leaflet support material was subsequently placed on the device assembly jig. FIG. 10A shows a cross-sectional, schematic view of the device assembly jig 1000 with coupon 960 lying atop and centered on the raised surface 1005. The raised surface 1005 has an outer edge that corresponds to the frame 554 so that the frame 554 can be seated around the raised surface 1005. The frame 554 was placed on top of the coupon 960 about the raised surface 1005 so that the coupon edges were either generally parallel or generally perpendicular with the bridge 556. As shown, a first coupon edge 962 and a second coupon edge 964 opposite the first coupon edge 962 was generally parallel with the bridge 556. Any wrinkles in the portion of the coupon 960 within the frame 554 were removed. The shaped fiber 940 (as shown in FIG. 9A) was set atop the bridge 556 on the device assembly jig 1000 such that a mid-portion 942 of the fiber 940 straddled the bridge 556 and a first base portion 944 and a second base portion 946 of the fiber 940 rested on the coupon 960 within the central opening 558 of the frame 554.

A first reinforcement 850a was positioned on top of the first base portion 944 and a second reinforcement 850b was positioned on top of the second base portion 946. The first coupon edge 962 and the second coupon edge 964 were folded inward so as to completely cover the first reinforcement 850a and the second reinforcement 850b, and trimmed parallel with the bridge, as shown in FIG. 10A.

Figure 10B:
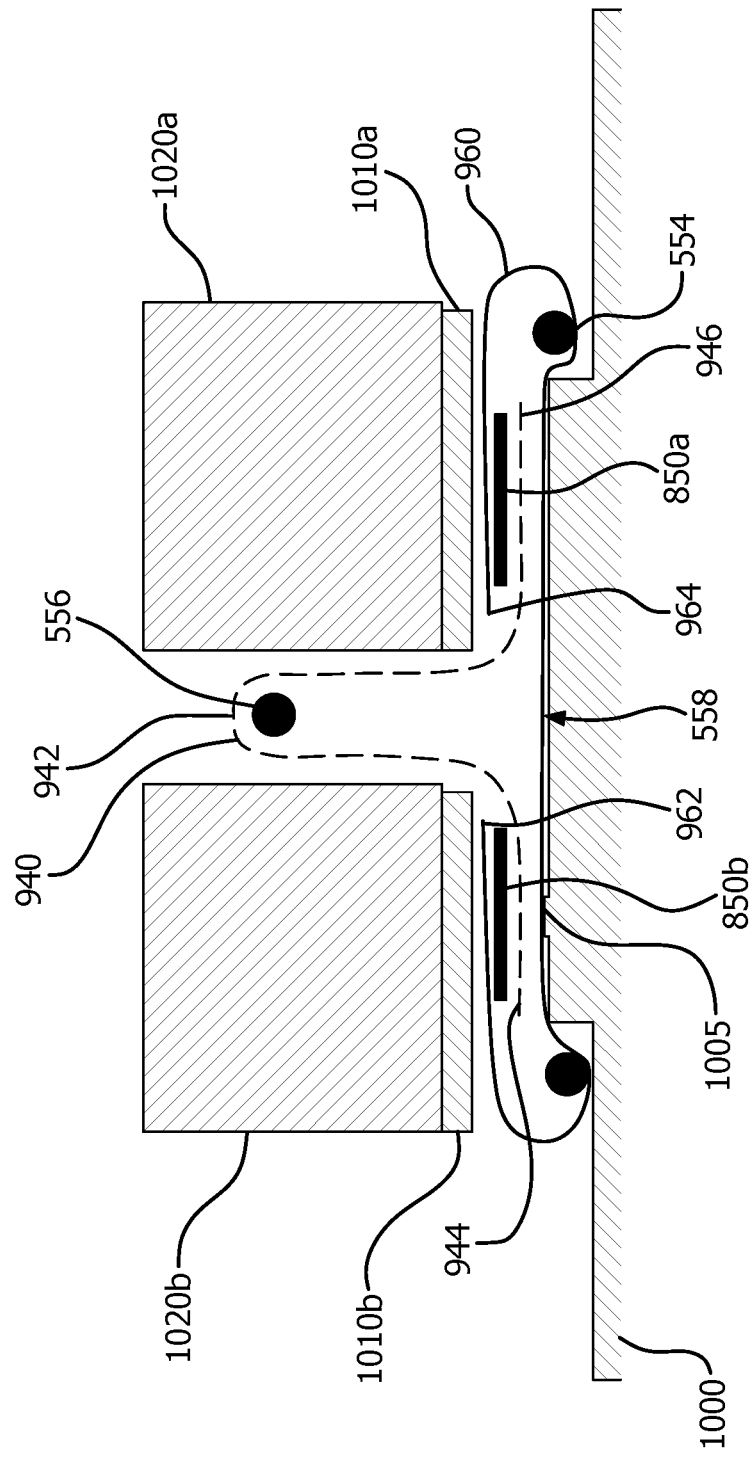
FIG. 10B is a cross-sectional, schematic view of a device assembly jig with the components layered on the jig with block presses set atop the device assembly jig.

To bond the stacked and wrapped components together, with reference to FIG. 10B, a first ePTFE cushion pad 1010a and a second ePTFE cushion pad 1010b were placed atop the layered coupon 960 and flanking the bridge 556. Atop the first ePTFE cushion pad 1010a and the second ePTFE cushion pad 1010b, a first tooling block 1020a and a second tooling block 1020b were placed as shown in FIG. 10. The device assembly jig 1000, the folded coupon 960, the frame 554, the shaped fiber 940, the first reinforcement 850a and the second reinforcement 850b, the first ePTFE cushion pad 1010a, the second ePTFE cushion pad 1010b, the first tooling block 1020a, and the second tooling block 1020b were compressed with a force of about 1560 N and heated for about 30 min in a press in which both platens were heated to about 260° C.

The resultant bonded coupon 960, the frame 554, the shaped fiber 940, the first reinforcement 850a and the second reinforcement 850b, the first ePTFE cushion pad 1010a, the second ePTFE cushion pad 1010b, the first tooling block 1020a, and the second tooling block 1020b were removed from the press and allowed to cool. The first tooling block 1020a, the second tooling block 1020b, the first ePTFE cushion pad 1010a, and the second ePTFE cushion pad 1010b were removed.

Figure 11:
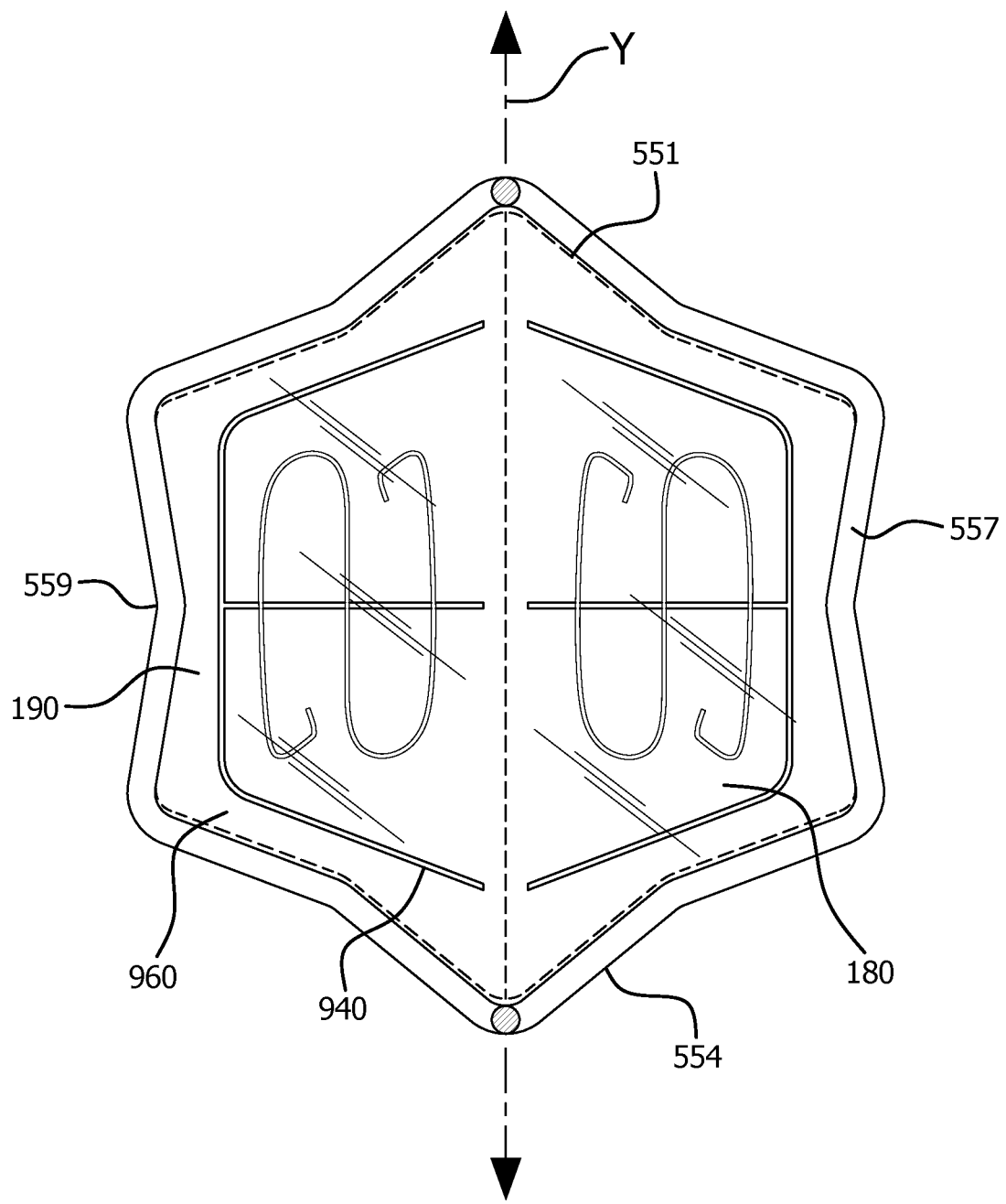
FIG. 11 is an outflow side, top view of a leaflet support device with dashed lines showing the lines where the leaflet support material is cut to form the support leaflets.

As demonstrated in FIG. 11, when the frame 554 is oriented such that the bridge (not shown) extends along a Y-axis between 0° and 180°, the coupon 960 was cut along the inner perimeter 551 of the frame 554 except for a first frame section 557 between 60° to 120° and a second frame section 559 between 240° to 300°. A cut was then made to the coupon 960 along the Y-axis in between the vertical portions 947 (shown in FIG. 9A) of the shaped fiber 940. Excess material was trimmed to create a first leaflet support 180 and a second leaflet support 190.

The resulting mitral leaflet support device was examined to demonstrate proper function. The support leaflets opened in the direction of blood flow and were restrained from prolapse by the tether.

Example 2

Another mitral leaflet support device was formed as described in Example 1, using the same materials, with a few exceptions. The exceptions stem from a different limiter design which does not comprise the shaped fiber as a tether and also has no elevated bridge.

The frame was prepared with a serpentine wire winding performed in a single direction consisting of six 360° passes around the pins, without the creation of a bridge. Consequently, tooling blocks were unnecessary.

In this example, the limiters were added after the bonding and cutting step which formed the two support leaflets. The limiter design of this example is a straight bridge that extends across the central opening and sits generally in the plane thereof. To form the limiters, the support leaflets were set in an open position. An ePTFE fiber was wrapped 6 times about the frame and the central opening. The wrapped fiber extended across the central opening in a direction that is generally parallel with a line defined by a central portion of the leaflet free-edge. Moreover, the wrapped fiber was positioned such that it would contact the leaflet support about midway between the leaflet support base and the leaflet support free-edge when the leaflet support is in the closed position. The ends were terminated with a knot. The fiber wraps were covered with 3 layers of a helical wrap of the above-described second composite and the composite was adhered together by rubbing with a soldering iron set to about 360° C.

The resulting mitral leaflet support device was examined to demonstrate proper function. The leaflet supports opened in the direction of blood flow and were restrained from prolapse by the straight bridge.

Example 3

Another mitral leaflet support device was formed as described in Examples 1 and 2, using the same materials and methods. This example discloses an embodiment having an improved atrial fixation system.

A three dimensional jig was designed on which to mount the nitinol wire for the construction of the atrial fixation struts. Nitinol wire (Fort Wayne Metals, Fort Wayne IN, nominal diameter 0.322 mm) was obtained, electropolished to a diameter of 0.317 mm, and heat treated in air to obtain a straight configuration. The jig was wound with two complete circuits of the wire, the wire restrained in place and the jig assembly placed in a forced air oven at 380 centigrade for 10 minutes. It was then water-quenched and removed from the jig. Two of the atrial struts were overlapped for mechanical continuity.

A second wire jig was used to form an interlocking base for the assembly. The two frames were then interlocked and sutured together with CV5 ePTFE suture.

The base of the two interlocked frames serves as the surface against which the augmentation leaflet can coapt and is located at the level of the mitral annulus. A monolayer leaflet of ePTFE and fluoroelastomer was constructed.

As used herein, the term "monolayer" refers to a construct consisting of a single ply of a thin sheet of material. One example of a monolayer is a single ply of a thin sheet of expanded PTFE. This expanded PTFE then may or may not be raised to a temperature at or above the crystalline melt temperature of PTFE. Another example of a monolayer is a single ply of a thin sheet of expanded polyethylene.

As used herein, the term "monolayer" refers to a construct consisting of a single ply of a thin sheet of material. One example of a monolayer is a single ply of a thin sheet of expanded PTFE. This expanded PTFE then may or may not be raised to a temperature at or above the crystalline melt temperature of PTFE. Another example of a monolayer is a single ply of a thin sheet of expanded polyethylene.

In one embodiment, the elastomer that is combined with the ePTFE is a thermoplastic copolymer of tetrafluoroethylene (TFE) and perfluorom ethyl vinyl ether (PMVE), such as described in U.S. Pat. No. 7,462,675. As discussed above, the elastomer is combined with the expanded fluoropolymer membrane such that the elastomer occupies substantially all of the void space or pores within the expanded fluoropolymer membrane. This filling of the pores of the expanded fluoropolymer membrane with elastomer can be performed by a variety of methods.

With a third wire jig and using the methods already described, a serpentine NiTi wireform element was constructed to serve as leaflet reinforcement. The wire was formed into a horseshoe shape and heat-treated. FEP powder (Daikin America, Orangeburg N.Y.) was then applied to the shaped bundle 553. More specifically, the FEP powder was stirred to form an airborne "cloud", while the wire assembly was suspended in the cloud. The shaped bundle 553 was removed and momentarily placed in a forced air oven set to 320° C. in order to bond the powder to the serpentine wireform. This reinforcement was then bonded to the reinforcing leaflet and the leaflet sewn to the interlocked frame elements.

While this embodiment has only one leaflet (anterior) it could have a second leaflet, one leaflet and a prosthetic coaptation surface, or only a coaptation surface when no prolapse is present in the native valve.

Methods: The above described physical characteristics of the materials used can be determined according to the following methods. However, it should be understood that any method or equipment determined suitable by one of ordinary skill in the art may be alternatively utilized.

Thickness: The thickness of films and membranes was measured by placing the membrane between the two plates of a Kafer FZ1000/30 thickness snap gauge Kafer Messuhrenfabrik GmbH, Villingen-Schwenningen, Germany. For thin membranes, multiple layers were measured at one time and the thickness of a single membrane was obtained by dividing the measured thickness by the number of layers measured. It should be appreciated that any suitable method for measuring thickness may be used.

Density & Mass per Area: The density and mass per area are properties of membranes. An analytical balance (Mettler PM400 New Jersey, USA) was used to determine the mass of a sample of known area. Density was calculated with the following formula: $\rho=m/A*t$, in which: $\rho$=density, m=mass, A=area, and t=thickness. Mass per Area was calculated by dividing the mass by the sample area.

Tensile Strength of ePTFE Membranes: The Matrix Tensile Strength (MTS) of membranes was measured by first measuring the maximum tensile force of the membrane using an Instron 122 tensile test machine (Instron, Norwood, MA) equipped with flat grips and an 0.445 kN load cell. The gauge length was about 5.08 cm and the cross-head speed was about 50.8 cm/min. The sample dimensions were about 2.54 cm by about 15.24 cm. The matrix tensile strength, MTS, was calculated from the tensile strength and density according to the equation: MTS=(maximum tensile force/cross-section area)*(bulk density of PTFE)/(density of the porous membrane), wherein the bulk density of the PTFE was taken to be about 2.2 g/cm$^3$.

Numerous characteristics and advantages have been set forth in the preceding description, including various alternatives together with details of the structure and function of the devices and/or methods. The disclosure is intended as illustrative only and as such is not intended to be exhaustive. For example, embodiments of the present disclosure are described in the context of medical applications but can also be useful in non-medical applications. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:
1. A leaflet support device, comprising:
a first frame defining a base, a tubular member, and a first frame central opening;
a second frame defining a flat ring, a second frame central opening, and an inner portion, the second frame coupled to the base of the first frame;

a support leaflet including a leaflet attachment region coupled to the base of the first frame and a leaflet free edge opposite the leaflet attachment region, the support leaflet configured to transition between an open position and a closed position, the inner portion of the second frame operable to limit movement of the support leaflet when transitioning from the open position to the closed position.

2. The leaflet support device of claim 1, wherein the first frame and the second frame are positioned coaxially.

3. The leaflet support device of claim 1, wherein the first frame has a decreasing taper from a first end to the base.

4. The leaflet support device of claim 1, wherein the first frame is operable to conform to and be coupled with an atrial side of a heart adjacent to an atrioventricular valve.

5. The leaflet support device of claim 1, wherein the second frame defines an outer portion extending away from the first frame central opening.

6. The leaflet support device of claim 5, wherein the outer portion of the second frame is operable to be positioned against an upstream side of an annulus of an atrioventricular valve.

7. The leaflet support device of claim 1, wherein the support leaflet is operable to support at least a portion of an atrial-facing surface of an atrioventricular valve leaflet when in the closed position.

8. The leaflet support device of claim 1, further comprising a second support leaflet, wherein the support leaflet and the second support leaflet are sized such that the support leaflet and the second support leaflet do not overlap with each other when in the closed position.

9. The leaflet support device of claim 1, further comprising a second support leaflet, wherein the support leaflet has a larger surface area than the second support leaflet.

10. The leaflet support device of claim 1, wherein the support leaflet has a size suitable to cover at least half of a non-coapting portion of an atrial-facing surface of a respective atrioventricular valve leaflet, when the atrioventricular valve leaflet is in the closed position.

11. The leaflet support device of claim 1, wherein a portion of the support leaflet between the leaflet attachment region and the free edge comprises a polymer configured for cellular ingrowth and defining at least a portion of a ventricular-facing surface.

12. The leaflet support device of claim 1, wherein the support leaflet comprises one or more stiffer regions with a stiffness that is greater than an adjacent region.

13. The leaflet support device of claim 12, wherein the one or more stiffer regions with greater stiffness extend across at least 70% of a dimension of the support leaflet wherein the dimension is substantially transverse to blood flow.

14. The leaflet support device of claim 13, where the one or more stiffer regions with greater stiffness extends along a length that is in the same direction as a line defined by native leaflet coaptation.

15. The leaflet support device of claim 14, wherein the one or more stiffer regions is configured to abut with the inner portion of the second frame.

16. The leaflet support device of claim 1, wherein the first frame defines a plurality of petals or loop which extend at an angle to define a decreasing taper of the tubular member.

17. The leaflet support device of claim 1, wherein the first frame and second frame are configured to be resiliently compressible in a radial direction such that the first frame, when in a compressed state during use, urges against an annulus or an atrium to couple the first frame to the annulus or the atrium.

18. The leaflet support device of claim 1, further comprising a tether coupled to the support leaflet that is configured to be coupled to a ventricular structure.

19. The leaflet support device of claim 18, wherein the tether is suture, fiber, or thread.

20. A leaflet support device, comprising:
a first frame defining a base, a tubular member, and a first frame central opening;
a second frame defining a flat ring, a second frame central opening, and an inner portion, the second frame coupled to the base of the first frame;
a first support leaflet including a leaflet attachment region coupled to the base of the first frame, the first support leaflet configured to transition between an open position and a closed position, the second frame operable to limit movement of the support leaflet when transitioning from the open position to the closed position; and
a second support leaflet, wherein the first support leaflet and the second support leaflet are sized such that the first support leaflet and the second support leaflet do not overlap with each other when in the closed position.

21. A leaflet support device, comprising:
a first frame defining a base, a tubular member, and a first frame central opening;
a second frame defining a flat ring, a second frame central opening, and an inner portion, the second frame coupled to the base of the first frame;
a support leaflet including a leaflet attachment region coupled to the base of the first frame and a leaflet free edge opposite the leaflet attachment region, the support leaflet configured to transition between an open position and a closed position, the support leaflet including one or more stiffer regions with a stiffness that is greater than an adjacent region.

* * * * *